(12) United States Patent
Balin et al.

(10) Patent No.: US 7,189,703 B2
(45) Date of Patent: Mar. 13, 2007

US007189703B2

(54) TREATMENT AND DIAGNOSIS OF ALZHEIMER'S DISEASE

(75) Inventors: Brian J. Balin, Paoli, PA (US); J. Todd Abrams, Merion, PA (US); Alan P. Hudson, Novi, MI (US); Judith A. Whittum-Hudson, Novi, MI (US)

(73) Assignee: Intracell, LLC, Merion, PA (US)

( * ) Notice: Subject to any disclaimer, the term of this patent is extended or adjusted under 35 U.S.C. 154(b) by 0 days.

(21) Appl. No.: 09/227,749

(22) Filed: Jan. 8, 1999

(65) Prior Publication Data
US 2001/0014670 A1 Aug. 16, 2001

Related U.S. Application Data

(60) Provisional application No. 60/070,855, filed on Jan. 9, 1998.

(51) Int. Cl.
*A61K 31/56* (2006.01)
*A61K 31/65* (2006.01)
*A61K 31/70* (2006.01)

(52) U.S. Cl. .................. 514/29; 514/152; 514/179
(58) Field of Classification Search .............. 514/29, 514/152, 179
See application file for complete search history.

(56) References Cited

U.S. PATENT DOCUMENTS

| 4,419,365 | A | * | 12/1983 | McLachlan ............... 514/575 |
|---|---|---|---|---|
| 5,034,506 | A | | 7/1991 | Summerton et al. |
| 5,424,187 | A | * | 6/1995 | Shor et al. ............... 435/6 |
| 5,700,816 | A | | 12/1997 | Isakson et al. |
| 5,789,395 | A | | 8/1998 | Amin et al. |
| 5,846,220 | A | * | 12/1998 | Elsberry ............... 604/500 |
| 5,880,101 | A | * | 3/1999 | Stankov ............... 514/29 |
| 5,919,775 | A | | 7/1999 | Amin et al. |
| 6,255,347 | B1 | * | 7/2001 | Xiaotao et al. .......... 514/570 |
| 6,579,854 | B1 | * | 6/2003 | Mitchell et al. .......... 514/31 |
| 6,664,239 | B2 | * | 12/2003 | Mitchell et al. .......... 514/29 |

FOREIGN PATENT DOCUMENTS

WO WO 96/00576 * 1/1996

OTHER PUBLICATIONS

Abrams et al. ,1991, J. Immunol. 146:1455-1462.
Abrams et al., 1993, Cancer Res. 53:5501-5506.
Abrams et al. ,1991, J. Invest. Dermatol. 96:31-37.
Alonso et al., 1996, Nature Med. 2:783-787.
Andersen et al., 1995, Neurology 45:1441-1445.
Appelt et al., 1996, J. Histochem. Cytochem. 44:1421-1427.
Barbas, 1995, Nature Medicine 1:837-839.
Bird et al., 1988, Science 242:423-426.
Blacker et al., 1997, Neurol. 48:139-147.
Bolton et al., 1993, Ann. Neurol. 33:94-100.
Branigan et al., 1996, Arthritis Rheumat. 39:1740-1746.
Breitner et al., 1994, Neurology 44:227-232.
Breteler et al., 1992, Epidemiol. Rev. 14:59-82.
Bretschneider et al., 1981, Am. J. Clin Path. 76:450-453.
Burton and Barbas, 1994, Adv. Immunol. 57:191-280.
Campbell et al., 1995, J. Infect. Dis. 172:585-588.
Capron, 1996, Nature Med. 2:856-857.
Chakravarthy et al., 1995, Curr. Eye Res. 14:285-294.
Clark et al., 1993, Arch. Neurol. 50:1164-1172.
Connors et al., 1995, Stem Cells, 13:501-511.
Cook et al., 1996, Proc. Natl. Acad. Sci. USA 93:9223-9228.
Corder et al., 1993, Science 261:921-923.
de Kruif et al., 1995, J. Mol. Biol.248:97-105.
Evans et al., 1989, J. Amer. Med. Assn. 262:2551-2556.
Friedland et al., Arch. Neurol. 47:177-178.
Gautrin et al., 1989, Can. J. Neurol. Sci. 16:375-387.
Gaydos et al., 1992, J. Clin. Microbiol. 30:796-800.
Gran et al., 1993, Scand. J. Rheumatol. 22:43-44.
Grayston et al., 1993, J. Infec. Dis. 168:1231-1235.
Grayston, 1992, Ann.. Rev. Med. 43:317-323.
Grayston et al., 1990, J. Infect. Dis. 161:618-625.
Greenberg, 1990, Proc. Natl. Acad. Sci. USA 87:5827-5831.
Gu et al., 1997, Thrombosis and Hematocyst 77(4):755-759.
Hahn et al., 1991, J. Amer. Med. Assn. 266:225-230.
Hatch, 1998, Science 282:754-759.
Hixson et al., 1990, J. Lipid Res. 31:545-548.
Hofman et al., 1997, Lancet 349:151-153.
Huston et al., 1988, Proc. Natl. Acad. Sci. USA 85:5879-5883.
Itzhaki et al., 1997, Lancet 349:241-244.
Johnson, 1994, J. Neurol. Sci. 124:3-14.
Keefover, 1996, Neurol. Clin. 14:337-351.
Kingsbury et al., 1995, Mol. Brain Res. 28:311-318.
Koskiniemi et al., 1996, Eur. Neurol. 36:160-163.
Kurosaka et al., 1998, J. Immunol. 161:6245-6249.
Lee et al., 1991, Science 251:675-679.
Lee et al., 1996, J. Neurosci. 16:7513-7525.
Leinonen, 1993, Eur. Heart J. 14:57-61.
Lemere et al., 1996, Nature Med. 2:1146-1150.
Li et al., 1998, Cell Biol. Int. 22:13-20.
Li et al., 1996, Arthritis Rheumat. 39:950-958.
Lippa et al., 1996, Neurol. 46:406-412.
Löbau et al., 1995, Mol. Microbiol. 18:391-399.
Lomax et al., 1990, Gene 86:209-216.
Malinverni, 1996, Curr. Opin. Infect. Dis. 9:150-156.
Mann et al., 1983, Acta Neurol. 60:24-28.
Marks et al., 1991, J. Mol. Biol. 222:581-597.

(Continued)

*Primary Examiner*—Elli Peselev
(74) *Attorney, Agent, or Firm*—Caesar, Rivise, Bernstein, Cohen & Pokotilow, Ltd.

(57) ABSTRACT

The invention relates to a method of treating Alzheimer's disease in a mammal comprising administering to the mammal an anti-microbial agent having anti-*Chlamydia pneumoniae* activity. The invention also relates to a method of diagnosing Alzheimer's disease in a mammal comprising measuring the serum anti-*Chlamydia pneumoniae* antibody titer in a patient suspected of having Alzheimer's disease.

16 Claims, 18 Drawing Sheets

OTHER PUBLICATIONS

McKee et al., 1991, Ann. Neurol. 30:156-165.
McKhann et al., 1984, Neurology 34:939-994.
Mehta et al., 1998, J. Infect. Dis. 177:1326-1331.
Melgosa et al., 1991, Infect. Immunol. 59:2195-2199.
Melgosa et al., 1994, Infect Immun. 62:880-886.
Merrill et al., 1993, J. Immunol. 151:2132-2141.
Mirra et al., 1991, Neurology 41:479-486.
Miyashita et al., 1993, J. Med Microbiol. 38:418-425.
Montarras et al., 1994, In: The Polymerase Chain Reaction, Mullis et al., eds., Birkhäuser, Press, Boston, MA, pp. 277-294.
Muhlestein et al., 1996, J. Amer. Coll. Cardiol. 27:1555-1561.
Nielsen et al., 1991, Science 254:1497-1500.
Numazaki et al., 1995, J. Med. Microbiol. 42:191-195.
Peterson et al., 1998, Infect. Immun. 66:3848-3855.
Peterson et al., 1996, Infect. Immun. 64:3354-3359.
Pogo et al., 1987, Brain 110:907-915.
Poulakkainen et al., 1995, Microbiol. Immunol. 39:551-554.
Renvoize et al., 1987, Age and Ageing 16:311-314.
Rogers et al., 1993, Neurology 43:1609-1611.
Roses, 1996, Ann. Rev. Med. 47:387-400.
Schellenberg, 1995, Proc. Natl. Acad. Sci. USA 92:8552-8559.
Sriram et al., 1998, Neurol. 50:571-572.
Stagg, 1998, Mol. Med. Today 4:166-173.
Strugnell et al., 1997, Immunol. Cell Biol. 75:364-369.
Tuszynski et al., 1988, Blood, 72:109-115.
Waldman, 1991, Science 252:1657-1662.
Wang et al., 1996, Nature Med. 2:871-875.
Whittum-Hudson et al., 1996, Nat. Med. 2:1116-1121.
Wimmer et al., 1996, Stroke 27:2207-2210.
Wisniewski et al., 1988, Ciba Fdn. Sympos. 135:224-238.
Wong et al., 1992, J. Clinical Microbiol. 30:1625-1630.
Wright et al., 1992, Critical Rev. in Immunol. 12(3,4):125-168.
Yankner, 1996, Nature Med. 2:850-852.
Zhang et al., 1997, J. Infect. Dis. 176:1035-1040.
Jaruratanasirikul et al., Mar. 1996, "Distribution of Azithromycin Into Brain Tissue, Cerebrospinal Fluid, and Aqueous Humor of the Eye", *Antimicrobial Agents and Chemotherapy,* vol. 40, No. 3, p. 825-826.
Matthews, 1986, Neuropathology and Applie Neurobiology 12:111-116.
Morbidity and Mortality Weekly Report, CDC, 1993 Sexually Transmitted Diseases Treatment Guidelines, 42:No. RR-14.
Balin, Brian J. et al. "Identification and Localization of Chlamydia Pneumoniae in the Alzheimer's Brain," Med Microbiol Immunol, 187:23-42, 1998.
Mahony, James B. et al. "Identification of Chlamydia Pneumoniae in the Alzheimer's Brain," World Alzheimer Congress 2000, Pivotal Research, Washington, DC, Abstract 1120, Jul. 2000.
Habeck, M. "Infectious Link to Alzheimer's Disease," Targets, vol. 1, No. 5, p. 147, Dec. 2002.
Mahony, J. et al. "Chlamydia Pneumoniae in the Alzheimer's Brain—Is DNA Detection Hampered by Low Copy Number?," Proceedings Fourth Meeting of the European Society for Chlamydia Research, Helsinki-Finland, Clinical Diseases, p. 275, Aug. 2000.
Ossewaarde, J.M., et al. "Chlamydia Pneumoniae Antigens Are Present in the Brains of Alzheimer Patients, But Not in the Brains of Patients with Other Dementia's" Proceedings Fourth Meeting of the European Society for Chlamydia Research, Helsinki-Finland, Clinical Diseases, p. 284, Aug. 2000.

\* cited by examiner

TREATMENT AND DIAGNOSIS OF ALZHEIMER'S DISEASE

CROSS REFERENCE TO RELATED APPLICATIONS

This application claims priority under 35 U.S.C. § 119(e) to U.S. Provisional Application No. 60/070,855, filed on Jan. 9, 1998.

GOVERNMENT SUPPORT

This invention was supported in part by funds from the U.S. Government (NIH Grant Nos. AR-42541, EY-03324, and AG-10160) and the U.S. Government may therefore have certain rights in the invention.

FIELD OF THE INVENTION

The field of the invention is the treatment and diagnosis of Alzheimer's disease.

BACKGROUND OF THE INVENTION

Alzheimer's Disease (AD) is a severe mental health problem that affects an estimated 3–4 million people in the United States (Keefover, 1996, Neurol. Clin. 14:337–351). Many studies have established that AD appears in two distinct forms: an early-onset form and a late-onset, sporadic form. Incidence of the latter form increases with age, and AD is now believed to be the most important single cause of senile dementia in humans. Estimates of the prevalence of late-onset AD based on epidemiological evidence vary, and the incidence of the disease appears to differ with the population examined. However, at least half of the total cases of dementia in the elderly may be attributable to AD (Evans et al., 1989, J. Amer. Med. Assn. 262:2551–2556; Breteler et al., 1992, Epidemiol. Rev. 14:59–82). Thus, AD is a significant mental health concern, which is likely to increase in importance with the continued aging of the population.

The signature neuropathology seen in essentially all AD patients includes the presence in the brain of neurofibrillary tangles (NFT) and neuropil threads (NT) comprised of modified tau protein, and the presence of neuritic senile plaques (NSP) comprised of deposits of β-amyloid peptide (Aβ). The genesis of these neuropathologies is poorly understood. Tau protein is a normal component of the neuronal cytoskeleton, and evidence suggests that the abnormal deposition of this protein in NFT, NT, and dystrophic neurites results from aberrant post-translational modification of the protein (Lee et al., 1991, Science 251:675–679; Alonso et al., 1996, Nature Med. 2:783–787; Appelt et al., 1996, J. Histochem. Cytochem. 44:1421–1427; Wang et al., 1996, Nature Med. 2:871–875). It is not clear whether NFT represent primary lesions in AD, or whether the formation of these structures is a response to other neuronal injuries associated with the disease (Goedert, 1993, Trends Neurosci. 16:460–465). Some reports suggest that the level of NFT accumulation correlates most closely with the degree of cognitive impairment in AD patients (McKee et al., 1991, Ann. Neurol. 30:156–165).

Deposition of Aβ appears to be critical in the neuronal degeneration observed in AD (Schellenberg, 1995, Proc. Natl. Acad. Sci. USA 92:8552–8559). In the early-onset, familial form of AD (FAD), mutations in the amyloid precursor protein gene are associated with increased Aβ deposition and early onset of symptoms (Yankner, 1996, Nature Med. 2:850–852). Mutations in the genes encoding presenilin-1 (PS-1) and presenilin-2 (PS-2) also lead to increased Aβ deposition in FAD human patients and in an animal model system (Lemere et al., 1996, Nature Med. 2:1146–1150; Yankner, supra). Mutations in PS-1 and PS-2 and mutations in βAPP appear to account for most early-onset, FAD cases (Lee et al., 1996, J Neurosci. 16:7513–7525; Cook et al., 1996, Proc. Natl. Acad. Sci. USA 93:9223–9228).

Late-onset AD is more prevalent than early onset FAD. While early-onset FAD is almost certainly genetically-based, no such correlation has been established for late-onset AD. One risk factor identified in late-onset AD disease is the presence of the apolipoprotein E ∈4 (APOE ∈4) allele (Schellenberg, supra; Roses, 1996, Ann. Rev. Med. 47:387–400). Not all patients expressing the APOE ∈4 allele develop AD. However, the presence of this allele is associated with increased risk for the disease by several-fold and the allele is also associated with earlier onset/more rapid progression in FAD (Roses, supra; Corder et al., 1993, Science 261–921–923). A recent study suggests that expression of the APOE ∈4 allele may be a risk factor primarily in individuals younger than 70 years in age, and that it may be involved in only a minority of late-onset AD cases (Blacker et al., 1997, Neurol. 48:139–147).

The neuropathology characteristic of both early- and late-onset AD is similar, but the factors which initiate the pathology of late-onset AD remain to be elucidated (Clark et al., 1993, Arch. Neurol. 50:1164–1172; Lippa et al., 1996, Neurol. 46:406–412). Neurologic disease may be caused by microorganisms, and infection with agents that do not target the nervous system directly may elicit neuropathologic side-effects (Bolton et al., 1993, Ann. Neurol. 33:94–100; Johnson, 1994, J. Neurol. Sci. 124:3–14). In view of these reports, several groups have attempted to establish a causal relationship between viral infection and sporadic AD, but no etiologic link between the two has been unequivocally demonstrated. For example, measles virus, various lentiviruses, adenovirus and other infectious agents have been dismissed as potential agents associated with late-onset AD (e.g., Mann et al., 1983, Acta Neurol. 60:24–28; Friedlan et al., Arch. Neurol. 47:177–178; Pogo et al., 1987, Brain 110:907–915). Various bacterial species have also been evaluated and dismissed as potential agents associated with late-onset AD, including Chlamydia psittaci and Coxiella burnettii (e.g., Renvoize et al., 1987, Age and Ageing 16:311–314). One study identified herpes simplex virus type 1 (HSV-1) infection as a risk factor for development of AD in people expressing the APOE ∈4 allele (Itzhaki et al., 1997, Lancet 349:241–244), although it is not clear how and under what circumstances this virus might interact with the allele or its gene product to produce or promote disease. In addition to viruses and bacteria, unconventional agents (i.e., prions) have been considered but have been dismissed as agents in the pathogenesis of AD (Mathews, 1986, Neuropath. Appl. Neurobiol. 12:11–116; Wisniewski et al., 1988, Ciba Fdn. Sympos. 135:224–238). The possible roles of other factors, including diet and extended/acute exposure to aluminum, have also been investigated, but no definitive role for these factors in the etiology of AD has been demonstrated (Keefover et al., supra; Gautrin et al., 1989, Can. J. Neurol. Sci. 16:375–387).

Chlamydia pneumoniae (C. pneumoniae) is an intracellular bacterium that is a respiratory pathogen, initially infecting the oral and nasal mucosa of humans (Grayston et al., 1990, J. Infect. Dis. 161:618–625). This organism is a significant agent in acute respiratory infections of humans, including pneumonia, sinusitis, and bronchitis (Grayston et al., 1990, supra; Grayston, 1992, *Ann. Rev. Med.* 43:317–323). Recent studies have also implicated *C. pneumoniae* in more severe and chronic pulmonary pathologies, including sarcoidosis and chronic obstructive pulmonary disease (Hahn et al., 1991, *J. Amer. Med. Assn.* 266:225–230; Grayston et al., 1993, *J. Infec. Dis.* 168: 1231–1235). In addition, *C. pneumoniae* infection has been associated with multiple sclerosis and with meningoencephalitis (Sriram et al., 1998, Neurol. 50:571–572; Koskiniemi et al., 1996, Eur. Neurol. 36:160–163). Epidemiologic analyses have demonstrated that the prevalence of infection with *C. pneumoniae* is high in all adult populations studied, and that this prevalence increases with increasing age (Grayston, 1992, supra; Leinonen, 1993, *Eur. Heart J.* 14:57–61). In the Western world where population densities are relatively low, children under the age of 5 to 10 years rarely have anti-*C. pneumoniae* antibodies, but the incidence of the presence of antibodies rises sharply in these populations after the age of 10 (Grayston, 1992, supra; Leinonen, supra). *C. pneumoniae* antibody titers peak in the 6th–7th decades in most populations studied. For example, males 60 years and older in Seattle have a *C. pneumoniae* antibody prevalence rate of 70% (Grayston, 1992, supra; Leinonen, supra). All of the studies conducted to date indicate that virtually everyone is infected with *C. pneumoniae* during his or her lifetime, and that reinfection is common (Leinonen, supra).

Infection with *C. pneumoniae* has been implicated in unexpected clinical manifestations, including central nervous system disease and atherosclerosis (Gran et al., 1993, *Scand. J. Rheumatol.* 22:43–44; Campbell et al., 1995, *J. Infect. Dis.* 172:585–588; Koskiniemi et al., 1996, *Eur. Neurol.* 36:160–163; Muhlestein et al., 1996, *J. Amer. Coll. Cardiol.* 27:1555–1561). A correlation between central nervous system disease, primarily encephalitis, and serologically confirmed infection with *C. pneumoniae* has been found (Koskiniemi et al., supra). A significant correlation between serum anti-*C. pneumoniae* antibody titers and coronary artery disease has been established and the bacterium has been identified by electron microscopy and other methods in atheromatous plaques (Muhlestein et al., supra; Capron, 1996, *Nature Med.* 2:856–857). A significant correlation between serum anti-*C. pneumoniae* antibody titers and cerebrovascular disease has also been established (Wimmer et al., 1996, *Stroke* 27:2207–2210). A recent report postulated a relationship among atherosclerosis, APOE ∈4 expression, and late-onset AD (Hofman et al., 1997, *Lancet* 349:151–153). A direct correlation between *C. pneumoniae* infection and AD has not been suggested.

Alzheimer's disease is a significant health concern and it is likely to increase in importance with the continued aging of the population. Effective methods for the treatment or prevention of AD are not currently available and there is a long felt need for such methods of treatment or prevention.

SUMMARY OF THE INVENTION

The invention includes a method of treating a *Chlamydia pneumoniae* infection of the central nervous system of a mammal, wherein the mammal does not exhibit symptoms of multiple sclerosis or meningoencephalitis. The method comprises administering to the mammal an anti-microbial agent having anti-*Chlamydia pneumoniae* activity wherein the anti-microbial agent inhibits infection of cells or inhibits growth or replication of the *Chlamydia pneumoniae* in the mammal, thereby treating the *Chlamydia pneumoniae* infection.

In one aspect, the anti-microbial agent is an antibiotic.

In a preferred embodiment, the antibiotic is selected from the group consisting of a fluoroquinolone, a sulfonamide, a tetracycline, and a macrolide antibiotic.

In another preferred embodiment, the antibiotic is selected from the group consisting of ciprofloxacin, ofloxacin, sulfamethoxazole, trimethoprim, doxycycline, minocycline, oxytetracycline, tetracycline, azithromycin, clarithromycin, dirithromycin, erythromycin and troleandomycin.

In yet a further preferred embodiment, the antibiotic is selected from the group consisting of azithromycin and doxycycline.

In another aspect, the mammal is a human.

In yet another aspect, the anti-microbial agent is administered to the human by a route selected from the group consisting of orally, systemically, intranasally and intrathecally.

The invention also includes a method of treating Alzheimer's disease in a mammal wherein the method comprises administering to the mammal an anti-microbial agent having anti-*Chlamydia pneumoniae* activity wherein the anti-microbial agent inhibits infection of cells or inhibits growth or replication of the *C. pneumoniae* in the mammal, thereby treating the Alzheimer's disease.

In one aspect, the anti-microbial agent is an antibiotic.

In a preferred embodiment, the antibiotic is selected from the group consisting of a fluoroquinolone, a sulfonamide, a tetracycline, and a macrolide antibiotic.

In another preferred embodiment, the antibiotic is selected from the group consisting of ciprofloxacin, ofloxacin, sulfamethoxazole, trimethoprim, doxycycline, minocycline, oxytetracycline, tetracycline, azithromycin, clarithromycin, dirithromycin, erythromycin and troleandomycin.

In yet another preferred embodiment, the antibiotic is selected from the group consisting of azithromycin and doxycycline.

In one aspect, the mammal is a human.

In another aspect, the anti-microbial agent is administered to the human by a route selected from the group consisting of orally, systemically, intranasally and intrathecally.

Also included in the invention is a method of treating Alzheimer's disease in a human patient wherein the method comprises administering to the mammal an anti-microbial agent having anti-*Chlamydia pneumoniae* activity, wherein the anti-microbial agent inhibits infection of cells or inhibits growth or replication of the *C. pneumoniae* in the mammal, the method further comprising administering to the patient an anti-inflammatory agent, thereby treating the Alzheimer's disease.

In one aspect, the anti-inflammatory agent is a non-steroidal anti-inflammatory agent.

In a preferred embodiment, the anti-inflammatory agent is selected from the group consisting of ibuprofen, phenylbutazone, indomethacin, sulindac, diclofenac, piroxicam, naproxen, ketoprofen, pirprofen, flurbiprofen, tiaprofenic acid, tolfenamic acid, and a COX-2 inhibitor.

Further included in the invention is a method of diagnosing Alzheimer's disease in a human patient suspected of having Alzheimer's disease, wherein the human does not exhibit symptoms of multiple sclerosis or menginoencephalitis. The method comprises obtaining a cerebrospinal fluid sample from the patient, determining whether the cerebral spinal fluid sample contains *Chlamydia pneumoniae*, wherein the presence of *Chlamydia pneumoniae* in the sample is an indication that the patient has Alzheimer's disease.

In addition, the invention includes an another method of diagnosing Alzheimer's disease in a human patient suspected of having Alzheimer's disease, wherein the human does not exhibit symptoms of multiple sclerosis or menginoencephalitis. The method comprises measuring the serum anti-*Chlamydia pneumoniae* antibody titer in a patient suspected of having Alzheimer's disease and comparing the serum anti-*Chlamydia pneumoniae* antibody titer in the patient with the mean serum anti-*Chlamydia pneumoniae* antibody titer in a population of control patients, wherein a higher serum anti-*Chlamydia pneumoniae* antibody titer in the patient compared with the mean serum anti-*Chlamydia pneumoniae* antibody titer is an indication that the patient has Alzheimer's disease.

In yet another aspect, the invention includes a method of diagnosing Alzheimer's disease in a human patient, the method comprising administering an anti-SAF antibody to the human and determining whether the anti-SAF antibody binds to central nervous system tissue in the human, wherein binding of anti-SAF antibody to central nervous tissue in the human is an indication that the human has Alzheimer's disease.

In one embodiment, the anti-SAF antibody is administered to the human intrathecally.

In another embodiment, the antibody is labeled with a detectable label and wherein binding of the antibody is assessed by detecting the label bound to the tissue.

Also included in the invention is an anti-SAF antibody molecule.

In one aspect, the antibody is selected from the group consisting of a monoclonal antibody and a synthetic antibody.

Also included is an ELISA kit comprising an anti-SAF antibody and an instructional material.

In addition, the invention includes a method of diagnosing Alzheimer's disease in a human patient, the method comprising detecting evidence of the presence of *C. pneumoniae* in an intranasal sample obtained from the patient, wherein when the presence of *C. pneumoniae* in the sample is an indication that the patient has Alzheimer's disease.

Further included is a method of identifying a candidate compound for treatment of Alzheimer's disease comprising incubating cells infected with *Chlamydia pneumoniae* in the presence or absence of a test compound and measuring the level of replication of the *Chlamydia pneumoniae* in the cells, wherein a lower level of replication of the *Chlamydia pneumoniae* in the presence of the test compound compared with the level of replication of the *Chlamydia pneumoniae* in the absence of the test compound, is an indication that the test compound is a candidate compound for treatment of Alzheimer's disease.

In one aspect, the cells are selected from the group consisting of monocytes/microglia, macrophages, oligodendroglia, astroglial and neuronal cells.

The invention further includes a neuronal cell infected with *Chlamydia pneumoniae*.

In addition, the invention includes a plurality of neuronal cells infected with *Chlamydia pneumoniae*.

DETAILED DESCRIPTION OF THE INVENTION

Figure 1:
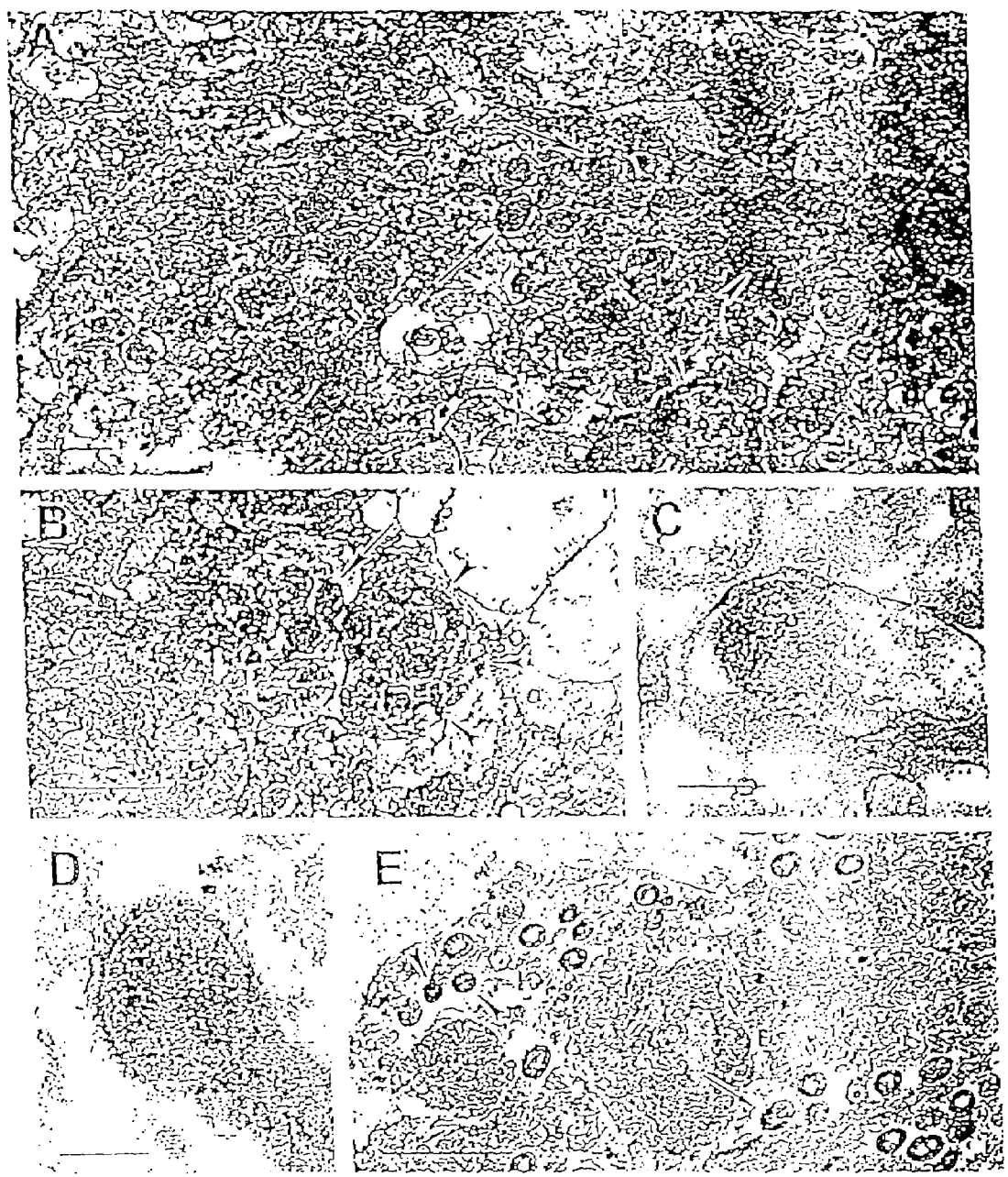
FIG. 1 is a series of images depicting electron microscopic (EM) and immunoelectron microscopic (IEM) analyses that identifies the elementary body (EB) and the reticulate body (RB) of *C. pneumoniae* in the brain tissues of AD patients that were PCR positive for *C. pneumoniae* DNA. Panel A is an EM image of the temporal cortex of patient AD8 depicting a typical inclusion body with presumptive EB and RB indicated by arrows and arrowheads, respectively (bar=0.5 µm). Panel B is an EM image of the temporal cortex of patient AD8 depicting inclusions (small arrowheads) in which a typical pear-shaped EB is found (arrow; bar=1.0 µm). Panel C is an IEM image of the temporal cortex of patient AD8 depicting an EB labeled with an anti-OMP monoclonal antibody (bar=0.1 µm). Panel D is an IEM image of the hippocampus of patient AD7, depicting an RB labeled with the anti-OMP monoclonal antibody (bar=0.25 µm). Panel E is an EM image of the hippocampus of patient AD7 depicting a disrupted inclusion body with pleomorphic forms of EB and RB indicated by arrowheads and arrows, respectively (bar=1.0 µm).

It has been discovered according to the present invention that *C. pneumoniae* infection of the central nervous system is associated with Alzheimer's disease. The pathology of Alzheimer's disease is characterized by inflammation of the brain, the deposition in the brain of β-amyloid peptides to form extracellular senile plaques (SP), and the intracellular accumulation of tau protein as paired helical filaments and neurofibrillary tangles. Without wishing to be bound by theory, it is believed that the infection of brain cells by *C. pneumoniae* contributes to the inflammatory process in the brain of the Alzheimer's patient and influences the aberrant synthesis and deposition of β-amyloid protein and/or tau protein in brain.

The invention relates to the treatment of a *C. pneumoniae* infection in the central nervous system of a mammal, preferably, a human, which mammal does not exhibit symptoms of either multiple sclerosis or meningoencephalitis. According to the invention, the mammal, preferably the human, being treated is administered an anti-microbial agent as disclosed herein, which agent inhibits the growth or replication of *C. pneumoniae* to reduce the same and thereby treat the infection in the human.

The symptoms of Multiple Sclerosis include those listed in any common medical textbook, including, for example, Gould, 1997, Pathophysiology for the Health Professions, W. B. Saunders Company. Symptoms of multiple sclerosis may include the following: motor weakness, spasticity, abnormal reflexes, impairment of vibratory/position sense, impairment of pain, temperature, touch, pain and Lhermitte sign, ataxia, tremor, nystagmus (brain stem or cerebellar) and Dysarthria (brain stem or cerebellar), affected vision, and ocular disturbances, etc. The symptoms of meningoencephalitis may also be found in any common medical encyclopedia, such as, for example, Gould (supra).

The invention further includes a method of treating Alzheimer's disease in a mammal, preferably a human, comprising administering to the mammal an anti-microbial agent capable of inhibiting growth and replication of *C. pneumoniae*, thereby ablating or alleviating *C. pneumoniae* infection in the mammal. By ablating or alleviating *C. pneumoniae* infection in the mammal, it is believed that the inflammatory processes in the brain associated with AD is diminished, thereby ablating or alleviating AD.

As used herein, AD is "alleviated" if the severity of a symptom of the AD, the frequency with which such a symptom is experienced by a patient, or both, are reduced.

As used herein, AD is "ablated" if the symptoms of AD have largely disappeared in the patient.

There is also included in the invention a method of preventing AD in a mammal comprising administering to a mammal known to be at risk for AD an anti-microbial agent capable of inhibiting growth and replication of *C. pneumoniae*, thereby preventing AD in the mammal. The types of compounds which may be used to prevent the onset of AD in a mammal are similar to those which may be used to alleviate or ablate AD in a mammal and are described in more detail further herein.

The invention further includes administering a *C. pneumoniae* vaccine to mammals at risk for AD as a means of preventing AD in these mammals. A *C. pneumoniae* vaccine may be an inactivated whole cell vaccine, or more preferably, the vaccine is a subunit vaccine comprising one or more antigens, which when introduced into a host mammal, preferably, induce an immune response which serves to inhibit/prevent or otherwise reduce or eliminate the growth and or replication of *C. pneumoniae* in the mammal. Such vaccines inlcude, but are not limited to a vaccine comprising *Chlamydia* OMP protein, *Chlamydia* LPS. In addition, the *C. pneumoniae* heat shock protein(s) (HSP) may also serve as candidate vaccines.

Further, as described in more detail elsewhere herein, it has been discovered in the present invention that an antibody, termed anti-SAF antibody, reacts with a protein, termed Sézary T-Cell Activating Factor (SAF), which is intimately associated with cells infected with *C. pneumoniae*. While not wishing to be bound by theory, it is believed that SAF reacts with a bacterial cell surface protein which in turn interacts with a eukaryotic cell surface receptor to which *C. pneumoniae* binds. Thus, SAF and antigenic fragments thereof, may also be used as vaccines candidates in the methods of the invention for treatment of *C. pneumoniae* in patients having AD.

The type of vaccine to be used is also not necessarily limited to the use of proteins, but rather, the vaccine to be used in the method of the invention may comprise nucleic acid, preferably, DNA. Examples of *Chlamydia* vaccines and methods of making the same are described in the art in the following references: Peterson et al., 1998, Infect. Immun. 66:3848–3855; Stagg. 1998, Mol. Med. Today 4:166–173; Zhang et al., 1997, J. Infect. Dis. 176:1035–1040; Strugnell et al., 1997, Immunol. Cell Biol. 75:364–369. Further, Whittum-Hudson et al. (1996, Nat. Med. 2:1116–1121) have developed an anti-idiotypic antibody directed against GLXA, an exoglycolipid of *Chlamydia* which functions to protect organisms against infection by *C. tracomatis*. Such a vaccine is useful in the present methods.

The invention also relates to a method of diagnosing AD, wherein the presence or absence of *C. pneumoniae* in the brain of a mammal suspected of having AD is assessed, the presence of *C. pneumoniae* being indicative of AD in the mammal. Such methods are described in more detail elsewhere herein.

Other methods which are included in the invention and are described in detail herein involve measurement of anti-*C. pneumoniae* antibody levels as a means of diagnosing AD in a mammal. These methods are also described in more detail elsewhere herein.

The term "Alzheimer's disease" as used herein, should be construed to include the pre-mortem definition of Alzheimer's disease as presented by the Alzheimer's Disease Education and Referral (ADEAR) Center—A service of the National Institute on Aging. This definition states "Alzheimer's disease is the most common type of dementia. This brain disorder usually develops gradually and the course of the disease can range from a few years to more than twenty years. Alzheimer's disease is irreversible. There is currently no cure for this disease." Dementia is defined as a general loss of intellectual abilities involving impairment of memory, judgement, and abstract thinking, as well as changes in personality. The diagnostic criteria for Alzheimer's disease adopted from the National Institute of Neurological Disease and Stroke and the Alzheimer's Disease and Related Disorders Association (NINCDS-ADRDA) Work group (McKhann et al., 1984, Neurology 34:939–994) are the following: (1) Probable AD—the typical disorder diagnosed clinically, unaccompanied by other recognized causes of dementia; (2) Possible AD—when AD is believed on clinical grounds to be responsible for dementia, but either atypical features (e.g., disproportionately severe language dysfunction) or other disorders able to impair cognition (e.g., stroke) are present; (3) Definite AD—for the histologically verified disorder.

The post-mortem definition of Alzheimer's disease is based on the occurrence in the Alzheimer's brain of several markers including senile plaques, which are dense cores of amyloid that form outside nerve cells, and neurofibrillary tangles which are tangled bundles of filaments found inside cells. Tangles comprise the normal brain protein, tau. These markers are concentrated in areas of the brain known to be important in learning, memory and language. A detailed description of Alzheimer's disease is provided in Mirra et al. (1991, Neurology 41:479–486).

By "treating", as used herein, is meant any therapy rendered to a mammal, preferably a human, for the purpose of preventing, alleviating, or ablating Alzheimer's disease, whether or not clinical symptoms of the disease are present in the mammal.

"Anti-microbial agent", as used herein, is meant any agent having anti-*C. pneumoniae* activity, including bacteriocidal or bacteriostatic activity. Such agents are those which prevent infection of cells by *C. pneumoniae* and those which inhibit growth and/or replication of *C. pneumoniae*. Such agents include traditional antibiotics known to be effective against *C. pneumoniae*, for example, but not limited to, the following groups of agents for treatment of chlamydial infection.

Fluoroquinolones are broad spectrum anti-infectives that are active against a wide range of aerobic gram positive and gram negative organisms. Preferred antichlamydial agents in this class of compounds are Ciprofloxacin and Ofloxacin, which are particularly effective against *C. trachomatis*. In fact, Ofloxacin is an accepted treatment for chlamydial infections of the endocervix and urethra (U.S. Pharmacopeia Dispensing Information, Volume 1, Drug Information for the Health Care Professional, 1996). In addition, Maxaquin and Trovan may also be used in the methods of the invention.

Also included are sulfonamides. These compounds are active in vitro against a broad spectrum of gram positive and gram negative bacteria. They are an accepted treatment for chlamydial infections of the endocervix and urethra (U.S. Pharmacopeia Dispensing Information, Volume 1, Drug Information for the Health Care Professional, 1996).

In addition, sulfamethoxazole and trimethoprim are used in combination for treatment for chlamydial infections (U.S. Pharmacopeia Dispensing Information, Volume 1, Drug Information for the Health Care Professional, 1996).

Tetracyclines are also useful for treatment of Chlamydial infections, in particular for treatment of Psittacosis caused by *C. psittaci* and for treatment of trachoma and genital infections of chlamydia. Doxycycline, minocycline, oxytetracycline and tetracycline may be included in a treatment regime against disease caused by chlamydia (U.S. Pharmacopeia Dispensing Information, Volume 1, Drug Information for the Health Care Professional, 1996). Of this class of antibiotics, doxycycline is the preferred antibiotic for treatment of Alzheimer's disease.

Also included are macrolides. These antibiotics are useful for treatment of chlamydial infections. Preferred antibiotics are azithromycin, clarithromycin, dirithromycin, erythromycin and troleandomycin. More preferred for treatment of chlamydial infections are azithromycin, clarithromycin and erythromycin (Drug Facts and Comparisons, 1977, 51st edition, Facts and Comparisons, 11 West Port Plaza, Suite 300, St. Louis, Mo.). Of this class of antibiotics, azithromycin is the preferred antibiotic for treatment of Alzheimer's disease.

The first line drugs of choice for treatment of chlamydial infection are doxycycline and azithromycin and thus these compounds are the preferred compounds for use in the methods of the invention.

Other anti-microbial agents useful for treatment of Alzheimer's disease include biological response modifiers and cytokines. For example interferon α and interferon γ may be used in the methods of the invention to affect a reduction in the replication of *C. pneumoniae* in a mammal, preferably, a human, thereby alleviating or ablating Alzheimer's disease in the human. The use of such biological response modifiers and cytokines to affect replication of *C. pneumoniae*, is known in the art and is described for example, in Malinverni (1996, Curr. Opin. Infect. Dis. 9:150–156) and in Mehta et al. (1998, J. Infect. Dis. 177:1326–1331). Antibodies which are directed against the mediators of inflammation are also potential therapeutic agents useful in the methods of the invention.

Also included are anti-microbial agents for treatment of Alzheimer's disease which include agents such as antisense nucleic acids, antibodies, small molecules, peptidometics and the like which have anti-*C. pneumoniae* activity.

With respect to antisense nucleic acids, oligonucleotides comprising sequences which are complementary to portions of *C. pneumoniae* genes which are essential for replication of the organism may be used to inhibit replication of the organism. Antisense technology is well known in the art and is described for example, in U.S. Pat. No. 5,034,506 and in Nielsen et al. (1991, Science 254: 1497). "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. Antisense oligonucleotide useful in the invention may include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No: 5,034,506; Nielsen et al., 1991, Science 254: 1497).

A likely effective oligonucleotide is one which inhibits an essential gene function in chlamydia, such as an oligonucleotide capable of inhibiting the KDO transferase gene or the heat shock protein, HSP72, gene of chlamydia, or genes involved in ATP transport in chlamydia. In addition, targets against which antisense molecules may be developed include the genes encoding proteins which are necessary and or facilitate infection of a cell by *C. pneumoniae*. Such genes include, but are not limited to, the gene encoding the outer membrane protein (OMP), the gene encoding the macrophage infection enhancing protein (MIP) and genes which encode proteo- and glycosaminoglycans. Additional targets include genes which encode crucial cell wall proteins and or porins which facilitate transport of ATP and nutrients into the bacterial cell (Hatch, 1998, Science 282:754–759; Peterson et al., 1996, Infect. Immun. 64:3354–3359; Lobau et al., 1995, Mol. Microbiol. 18:391–399).

With respect to antibodies, it is contemplated that antichlamydia antibodies which are capable of neutralizing the infectivity of this organism are included in the invention. Antibodies which are known in the art include the following: Mouse anti-*C. pneumoniae* antibody effective against the outer membrane protein of this organism. This antibody is designated as Clone No. RR402, Subclass IgG$_3$, Dako Diagnostics Limited, Carpinteria, Calif. (M6600) and/or Washington Research Foundation (#RR402); TWAR-specific monoclonal antibody, TT-410, subclass IgG, Dako Diagnostics Limited (K6101); *Chlamydia* ELISA Kit (IDEIA®*Chlamydia*), containing a genus-specific antibody to the chlamydia lipopolysaccharide antigen, Dako Diagnostics Limited (K6001 and 6002), (Christiansen et al., 1992, Europ. Microbiol. October 24–29; Grayson et al., 1990, J. Infect. Dis. 161(4):618–625; Wong et al., 1992, J. Clinical Microbiol. 30:1625–1630).

As discussed herein, antibodies which may be used in the method of the invention include any antibody having anti-*C. pneumoniae* activity. Preferably, the antibody is reactive against a cell surface component of chlamydia, such as, but not limited to, lipopolysaccharide (LPS). Also preferably, the antibody is reactive against an essential component of chlamydia, such as, but not limited to, the heat shock protein, HSP72. Antibodies which are useful in the methods of the invention include, but are not limited to, polyclonal and monoclonal antibodies, humanized antibodies, single chain antibodies, and phage expressed antibodies.

A preferred antibody for use in the methods if the invention is the anti-SAF antibody described in the Examples herein. While the generation of one particular anti-SAF antibody is exemplified herein, the invention should not be construed to be limited solely to this particular antibody, it being understood that upon a reading of the present invention, it is a simple matter for the skilled artisan to follow the directions provided herein and generate additional anti-SAF antibodies which are useful in the methods disclosed herein. The particular anti-SAF antibody disclosed in the Examples of the present disclosure is an IgG$_3$ mouse monoclonal antibody. This antibody was generated against a 28–30 kDA T cell mitogenic protein which was recovered from cutaneous lymphoma peripheral blood mononuclear cells and a cutaneous T cell lymphoma (CTCL) cell line. The antibody was selected based upon its neutralizing activity on SAF bioactivity. As described herein, this antibody functions in immunohistochemistry, immunoelectronmicroscopy, and immunocytochemistry to identify *C. pneumoniae* and *C. pneumoniae* proteins.

The present disclosure provides an example of the generation of an anti-SAF monoclonal antibody. Thus, the skilled artisan is capable of generating other antibodies which have anti-SAF activity based upon the disclosure provided herein. For example, it is possible to use a monoclonal cell line producing an anti-SAF antibody, as exemplified herein, to isolate nucleic acid which encodes the antibody. Nucleic acid encoding anti-SAF antibody may be cloned, and additional antibodies may be generated which comprise fragments of antibodies which have therapeutic or diagnostic value, or both. Such methods are described herein, and are also known to those skilled in the art.

The invention thus also includes an anti-SAF antibody, which antibody may be a poylclonal, a monoclonal or even a synthetic antibody as defined herein. Further, the invention should be construed to include the use of such an antibody in the methods of the invention and as a potential vaccine for the treatment of Alzheimer's disease.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988, Antibodies: A Laboratory Manual, Cold Spring Harbor, New York; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109–115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125–168) and the references cited therein. Further, the antibody of the invention may be "humanized" using the technology described in Wright et al., (supra) and in the references cited therein, and in Gu et al. (1997, Thrombosis and Hematocyst 77(4):755–759).

To generate a phage antibody library, a cDNA library is first obtained from mRNA which is isolated from cells, e.g., the hybridoma, which express the desired protein to be expressed on the phage surface, e.g., the desired antibody. cDNA copies of the MRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The MRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581–597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol.248:97–105).

The antibodies which are useful in the methods of the invention may be conjugated to cytotoxic agents such that attachment of the antibody to the *C. pneumoniae* cell will bring the cell into contact with a cytotoxic agent. Cytotoxic agents include but are not limited to chemotherapeutic agents, toxins, radioisotopes, and enzymes.

Chemotherapeutic agents to which an antibody may be conjugated include but are not limited to ricin, diphtheria toxin, and the like. In addition, it is possible to conjugate a KDO transferase inhibitor to such an antibody wherein only cells expressing KDO transferase and therefore only cells which are infected with chlamydia, will be killed. Antibodies having cytotoxic agents conjugated thereto are further described, for example, in Thorpe (1985, In: *Monoclonal Antibodies '84: Biological and Clinical Applications*; Pincherra et al., eds., Editrice Kurtis s.r.l.; Waldman, 1991, *Science* 252:16576–1662). The antibodies useful in the invention may also be conjugated to enzymes that catalyze the formation of cytotoxic chemicals at the site of antibody binding, as described, for example, in Connors et al. (1995, *Stem Cells,* 13:501–511).

Radioisotopes to which an antibody may be conjugated include but are not limited to $^{131}$I, $^{201}$Th and $^{99}$Tc. Conjugation of radioisotopes to antibodies is well known in the art and is described for example, in Harlow (1988, Antibodies: A Laboratory Manual. Cold Spring Harbor Laboratory, N.Y.).

It is important for treatment of Alzheimer's disease that the compound being used is capable of crossing the blood brain barrier. To accomplish this, the agent being used may be lipid soluble or may be formulated in a lipid soluble carrier or may be formulated such that it is transported across the blood brain barrier via a receptor-mediated transport mechanism. Alternatively, intrathecal delivery of the compound directly into the brain may be performed either via a ventricle or via spinal tap. In addition, the compound may be systemically administered to the individual in combination with mannitol which serves to transiently open the blood brain barrier thereby allowing the anti-chlamydial compound into the brain.

The agent may also be administered intranasally using a spray or aerosol.

By the term "anti-*C. pneumoniae* activity" as used herein as it refers to any of the anti-microbial agent discussed herein, is meant an agent having the activity of inhibiting growth or replication of, or inhibiting the infectivity or pathogenesis of *C. pneumoniae*. Growth and replication of *C. pneumoniae* may be assessed by PCR and reverse transcriptase PCR (RT-PCR), wherein the presence of chlamydia-specific RNA in cells is indicative of growth and replication of this organism. Growth and replication may also be assessed immunochemically using anti-outer membrane protein (OMP) and anti-LPS antibody. The infectivity and pathogenesis of chlamydia is assessed by assessing the ability of a test strain of chlamydia to infect cell lines comprising cells derived from brain tissue. Such cells include astrocytes, neuroblastomas and monocyte/microglia cell lines.

The exact protocol to be used in treating AD in a mammal by administering an anti-microbial agent to the mammal will be apparent to those skilled in the art and will vary depending upon the type and degree of the disease, the type and age of the mammal, and the particular anti-microbial agent being administered.

Treatment regimes for Alzheimer's disease which are contemplated include a single dose or dosage which is administered hourly, daily, weekly, monthly, or yearly. Dosages may vary and will include a dose of between about 1 ng/kg/day and 500 mg/kg/day. The route of administration may also vary depending upon the anti-microbial agent, the type and degree of the disease, and the type and age of the mammal. The anti-microbial agent is prepared for administration by being suspended or dissolved in a pharmaceutically acceptable carrier such as phosphate buffered saline, or other saline or salt solution, or other pharmaceutically acceptable carrier apparent to those skilled in such administration. The anti-microbial agent may be administered to a mammal in one of the traditional modes (e.g., orally, parenterally, transdermally or transmucosally or intrathecally), in a sustained release formulation using a biodegradable biocompatible polymer, or by on-site delivery using micelles, gels and liposomes, or rectally (e.g., by suppository or enema) or nasally (e.g., by nasal spray). Thus, the anti-microbial agent may be administered to the mammal by any route that facilitates access of the antimicrobial agent to the target site in the mammal, i.e. the site of *C. pneumoniae* infection in the brain or the site of *C. pneumoniae* infection any where in the body which may lead to infection of the brain. The appropriate pharmaceutically acceptable carrier in which the anti-microbial agent is suspended will be evident to those skilled in the art and will depend upon the anti-microbial agent and the route of administration.

As described herein, a number of agents have been approved by the Food and Drug Administration for use against chlamydia infections. In particular, the macrolide antibiotic, Azithromycin, has been used for treatment of respiratory disease caused by this organism. Recommended doses of Azithromycin are about 500 mg in a single orally administered dose followed by administration of 250 mg once daily for about four more days. Other recommended doses include a single oral dose of 1 g for treatment of sexually transmitted diseases attributable to chlamydia (CDC: 1993, Sep. 24, Vol. 42 (No. RR-14): 1–102). While it may be preferable to administer anti-chlamydia agents intrathecally or systemically when treating Alzheimer's disease, it will be appreciated that it is well within the skill of one in the art to determine the precise concentration and frequency of administration of such compounds to a patient having Alzheimer's disease.

Treatment of Alzheimer's disease with an anti-microbial agent may be accomplished in conjunction with other known and as yet unknown methods of treating Alzheimer's disease. For example, non-steroidal anti-inflammatory drugs (NSAIDs) have been examined for their affect on individuals at risk for Alzheimer's disease. While there is at present no defined or prescribed policy for treatment of Alzheimer's disease with anti-inflammatory agents, the results of some studies indicate a possible protective effect of NSAIDs on the onset of Alzheimer's disease (Andersen et al., 1995, *Neurology* 45:1441–1445). In a small, double-blinded, randomized trial study, reduced progression of Alzheimer's disease was observed in patients treated with indomethacin (Rogers et al., 1993, *Neurology* 43:1609–1611). Further, in yet another study involving twins, it has been suggested that NSAIDs or corticosteroids may reduce the risk of Alzheimer's disease in individuals identified as being at risk (Breitner et al., 1994, *Neurology* 44:227–232). Thus, treatment of Alzheimer's disease using anti-chlamydial agents in conjunction with anti-inflammatory agents is contemplated in the present invention. Such anti-inflammatory agents include, but are not limited to, ibuprofen, phenylbutazone, indomethacin, sulindac, diclofenac, piroxicam, naproxen, ketoprofen, pirprofen, flurbiprofen, tiaprofenic acid and tolfenamic acid. In addition, such anti-inflammatory agents may include specific COX-2 inhibitors which are known in the art, or which are heretofore unknown.

In the method of treating Alzheimer's disease in a patient using a combination of an anti-microbial agent and an anti-inflammatory agent, it is not necessary that both types of agents be administered simultaneously to the patient although simultaneous administration of both types of agents is contemplated as part of the present invention. However, it is also contemplated that the method of the invention may be practiced by first administering one type of agent followed by administration of the second type of agent, in any order as determined by the skilled artisan versed in the treatment of Alzheimer's disease and the administration of such agents to humans. It is further contemplated that one type of agent may be administered to the patient for a different period of time or periods of time , i.e., different frequencies of administration, compared with the length of time(s) and frequency of administration of the second type of agent.

The invention thus contemplates the administration of an anti-microbial agent to a human for the purpose of preventing, alleviating, or ablating Alzheimer's disease. Essentially, a human is treated for Alzheimer's disease by intrathecal administration of an anti-chlamydial agent in conjunction with an anti-inflammatory agent at a concentration and frequency which resembles administration of these compounds in humans for treatment of other conditions. Preferably, individuals who are at risk for developing Alzheimer's disease are treated prior to the onset of symptoms. Such individuals may be monitored for the presence of anti-chlamydia antibodies, and more particularly, for alterations in anti-chlamydia antibody levels during the treatment period.

In another aspect of the invention, a method of diagnosing Alzheimer's disease in post-mortem brain tissue is also contemplated. The method entails the detection of *C. pneumoniae* in the brain tissue as a diagnostic indicator for Alzheimer's disease. Alzheimer's disease in post-mortem brain tissue is currently diagnosed using various morphological markers in brain tissue, including the presence of neurofibrillary tangles, neuropil threads, and neuritic senile plaques (Mirra et al., 1991, *Neurol.* 41:479–486). Detection of *C. pneumoniae* in brain tissue can be used in conjunction with other diagnostic indicators for Alzheimer's disease. Additionally, detection of *C. pneumoniae* in brain tissue can be used as a diagnostic indicator in cases where the disease has not progressed sufficiently enough to allow for diagnosis using standard criteria. Tissue samples may be obtained from any area of the brain, including the hippocampus, the temporal cortex, the parietal cortex, the frontal cortex, the prefrontal cortex or the cerebellum. Preferred areas are the hippocampus and the temporal cortex. The presence of *C. pneumoniae* in the brain tissue sample is assessed and if confirmed, is indicative of infection in the brain by *C. pneumoniae*. The presence or absence of chlamydia in the tissue sample may be assessed using PCR or well known immunological protocols as described herein.

Pre-mortem diagnosis of Alzheimer's disease is initiated when a patient exhibits the following symptoms: difficulty in performing familiar tasks, speech difficulties, disorientation, rapid mood swings, misplacing items, and the like. More definitive pre-mortem diagnosis of Alzheimer's disease essentially comprises the steps of obtaining cerebrospinal fluid (CSF) from a mammal suspected of having Alzheimer's disease. CSF so obtained is analyzed to determine whether *C. pneumoniae* is present in the sample, wherein the presence of *C. pneumoniae* in the sample is an indication that the patient has Alzheimer's disease.

The presence or absence of *C. pneumoniae* in CSF obtained from a mammal is assessed using any one or more of a variety of procedures such as, but not limited to, electron and immunoelectron microscopy, immunohistochemistry, detection of *C. pneumoniae* DNA or RNA by hybridization and/or PCR amplification, RT-PCR amplification, and detection of *C. pneumoniae* nucleic acids using the technique of in situ hybridization. Each of these methods is performed using technology which is well known in the art and which is described herein in the experimental examples section and in Sambrook et al., (1989, Molecular Cloning: A Laboratory Manual, Cold Spring Harbor, N.Y.).

PCR primers useful for detection of *C. pneumoniae* are described herein in the experimental examples section. Additional primers for this purpose may be designed using techniques which are well known in the art. Briefly, primers which hybridize with either *C. pneumoniae* DNA or RNA, and which are preferably at least about 15 base pairs in length, may be designed based on a knowledge of the DNA sequence of *C. pneumoniae* and RNA expressed therefrom. Primers so designed are analyzed for sequence specificity via "Blast" comparison with DNA data bases are then tested extensively to establish that the use of these primers in a PCR amplification system specifically amplifies *C. pneumoniae* DNA or RNA.

In addition, any number of antibodies, either polyclonal or monoclonal antibodies may be used to detect the presence of *C. pneumoniae* in a tissue sample, including, for example, an antibody to the outer membrane protein (OMP) of *C. pneumoniae* (clone RR402, Poulakkainen et al., 1995, *Microbiol. Immunol.* 39:551–554; Washington Research Foundation, Seattle Wash.) and an anti-LPS antibody. In addition, the anti-SAF antibody of the invention may also be used to detect *C. pneumoniae* as described in the Examples provided herein, wherein data which establish colocalization of the anti-SAF antibody of the invention with *C. pneumoniae* in the brain are presented.

Further, the anti-SAF antibody of the invention may be used to identify SAF-like molecules and may ultimately be useful for the generation of SAF antagonists using technology readily available in the art upon a reading of the present disclosure.

In another aspect of the invention, a method of diagnosing Alzheimer's disease in a living human is also contemplated. As described herein, analysis of serum samples of patients who do not have AD (control patients) and patients having AD, establishes that patients having AD have a somewhat higher titer of anti-*C. pneumoniae* antibodies in their serum when compared with the level of serum anti-*C. pneumoniae* antibodies in control patients. The method of diagnosing Alzheimer's disease in a living human comprises the steps of measuring the level of serum anti-*C. pneumoniae* antibodies in a population of control patients to establish a baseline level of serum anti-*C. pneumoniae* antibodies in these patients. The level of serum anti-*C. pneumoniae* antibodies in a test patient suspected of having AD is also measured and is compared with the baseline level. A level of serum anti-*C. pneumoniae* antibodies in the test patient which is significantly higher than that of the baseline level is indicative that the patient has Alzheimer's disease. By the term "significantly higher" as used in the context of the aforementioned diagnostic assay, is meant at least about a 3-fold to about a four-fold higher level of serum anti-*C. pneumoniae* antibodies.

A baseline level of antibody titer is established by measuring the anti-*C. pneumoniae* antibody titer in a large number of non-demented, healthy control patients, matched in age range with the test patient. Serum is obtained from at least twenty such patients and the mean anti-chlamydia antibody titer is established using the procedures described herein for measurement of anti-chlamydia antibody titer. The term "baseline" level of antibody is used herein synonymously with the term "mean" antibody titer.

Serum anti-*C. pneumoniae* antibody titer may be established using any enzyme immunoassay for antigen detection. In addition, an SAF-based ELISA may be developed according to the invention, which uses affinity purified *C. pneumoniae* as the target in the assay. Affinity purification of SAF is accomplished using the anti-SAF antibody of the invention.

Diagnosis of Alzheimer's disease may also be accomplished by administering an anti-SAF antibody to the human and determining whether the anti-SAF antibody binds to central nervous system tissue in the human, wherein binding of anti-SAF antibody to central nervous tissue in the human is an indication that the human has Alzheimer's disease. The anti-SAF antibody may be administered to said human intrathecally, and in addition, the antibody may be labeled with a detectable label. In the latter instance, binding of the antibody is assessed by detecting the label bound to the tissue. Detectable labels include, but are not limited to, radionuclides such as $^{131}$I or Iridium. When these types of labels are used, the label is detected by radiodosimetry.

Kits for detection of antibodies using an ELISA may be developed and also are available commercially, for example, Mayo Medical Laboratories, Rochester, Minn. and Dako Corporation, Carpinteria, Calif. (*Chlamydia* ELISA Kit—IDEIA™*Chlamydia*). In addition, immunofluorescence assays may be used to detect chlamydia organisms in a tissue of fluid of a mammal. A kit for detection of a group chlamydial antigen is available from Mayo Medical Laboratories. Elevated titers indicate infection by a chlamydia which is either *C. trachomatis, C. psittaci* or *C. pneumoniae*. It is important to note that a single elevated IgG antibody titer directed against chlamydia does not necessarily connote recent infection with this organism. High immunofluorescent titers to chlamydiae may persist for several years, especially in adults. A four-fold or greater rise in anti-chlamydia antibody, as assessed by immunofluorescence, provides more definitive evidence of a recent chlamydia infection.

The invention thus also includes a kit comprising an antibody or other *Chlamydia*-detecting agent, preferably, the anti-SAF antibody of the invention, and an instructional material which describes adventitially using the kit to diagnose Alzheimer's disease in a human. In another embodiment, this kit comprises an ELISA assay suitable for the detection of *Chlamydia* in a sample obtained from a human and an instructional material for use of the kit.

As used herein, an "instructional material" includes a publication, a recording, a diagram, or any other medium of expression which can be used to communicate the usefulness of the kit for diagnosing Alzheimer's disease. The instructional material of the kit of the invention may, for example, be affixed to a container which contains the kit or be shipped together with a container which contains the kit. Alternatively, the instructional material may be shipped separately from the container with the intention that the instructional material and the kit be used cooperatively by the recipient.

Diagnosis of Alzheimer's disease may also be accomplished by detecting evidence of the presence of *C. pneumoniae* in an intranasal sample obtained from the patient. Samples of intranasal tissue and /or fluid are easily obtained and the presence of *C. pneumoniae* therein is assessed using any of the methods disclosed herein.

In another aspect of this invention, a method of identifying a therapeutic compound useful for the treatment of Alzheimer's disease is contemplated. The method involves incubating cells infected with *C. pneumoniae* in the presence or absence of a test therapeutic compound to determine if the compound possesses anti-*C. pneumoniae* activity directed against the intracellular form of the bacterium. A test compound has anti-*C. pneumoniae* activity if it affects the growth or replication of *C. pneumoniae* as described herein.

The types of cells which are useful in the assay include monocytes and macrophages and in particular, cell lines derived from the same. In addition, astroglial cells may be used which may be any cultured astroglial cells, including immortalized astrocytoma lines. Microglial cells oligodendroglia, and neuronal cells are also included.

The invention also includes a neuronal cell and a neuronal cell line, which cells are infected with C. pneumoniae, such cells being useful for the identification of compounds which are effective for inhibiting growth and/or replication of C. pneumoniae as described herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Identification and Localization of C. pneumoniae in the Alzheimer's Brain

The experimental example described herein provides procedures and results which establish that anti-microbial agent therapy is useful for the treatment of Alzheimer's disease since, according to the data provided herein, infection of brain tissue by C. pneumoniae is a contributing factor in the development or exacerbation of Alzheimer's disease.

Detection of C. pneumoniae Chromosomal DNA in the Alzheimer's Brain

Post mortem brain tissue from 19 late-onset AD patients and 19 non-AD control patients was examined using two different polymerase chain reaction (PCR) assays to determine whether C. pneumoniae DNA was present in the brains of late-onset AD patients. Postmortem brain tissue samples from patients with and without AD were obtained from the Harvard Brain Tissue Resource Center, the University of Alabama at Birmingham Brain Resource Center, the Medical College of Georgia (Augusta Ga.), and from the MCP-Hahnemann School of Medicine Dept. of Pathology. All samples from patients diagnosed as AD were confirmed at autopsy by histopathologic examination by a certified neuropathologist, using standard criteria (NINDS/CERAD) (Mirra et al., 1991, *Neurol.* 41:479–486). All AD patients had late-onset disease. Samples from non-AD patients were age matched as well as possible to those of AD patients, and each set was examined histologically for neuritic senile plaques (NSP) and neurofibrillary tangles (NFT) and confirmed as non-AD. The average age of control patients was 72.6 yr and that of AD patients was 77.7 yr.

For each AD and control patient, brain tissue obtained from one or more areas of the brain likely to have AD-related neuropathology and likely not to have AD-related neuropathology (in the latter case, the cerebellum) was screened for the presence of C. pneumoniae. Two independent PCR assay systems targeting two genes were used to screen for the presence of C. pneumoniae chromosomal DNA. In one assay system, primers targeting the 16S rRNA gene were used as described in Gaydos et al., 1992, *J. Clin. Microbiol.* 30:796–800. In a second assay system, primers targeting the chlamydial major outer membrane protein (MOMP) gene (omp1) were used.

MOMP primers derived from bases 26–43 and 567–548 (outer) and bases 115–135 and 444–462 (inner) of the C. pneumoniae MOMP coding sequence (Melgosa et al., 1991, *Infect. Immunol.* 59:2195–2199) were designed using GeneRunner® software (Hastings Software, Hastings N.Y.). The MOMP primers were analyzed for sequence specificity via "Blast" comparison with all DNA sequences in GenBank and were tested extensively for specificity for C. pneumoniae. Primers used in control PCR assays targeting sequences from C. trachomatis, Borrelia bergdorferi, Mycoplasma pneumoniae, and M. hominis were obtained as described in Branigan et al. (1996, *Arthritis Rheumat.* 39, 1740–1746) and Li et al. (1996, *Arthritis Rheumat.* 39:950–958). DNA obtained from the EB form of C. pneumoniae strain TW183 (ATCC) was prepared for use in control reactions.

The results of the PCR screening analysis for all patients are summarized in Tables 1–2. With one exception, all non-AD control samples were negative for the presence of C. pneumoniae DNA sequences as determined by PCR analysis, including those obtained from patients having multiple sclerosis (Table 1). The one exception was patient C1, wherein the parietal cortex sample exhibited a positive result. Of the 19 late-onset AD patients, samples obtained from 17 patients (90%) were PCR-positive in assays examining hippocampus, temporal cortex, and/or other areas (Table 2). Nucleic acids isolated from the cerebellum of 4AD patients (AD9, AD10, AD16, AD19) were also PCR-positive for C. pneumoniae DNA; each of these tissue samples exhibited severe neuropathology in histological examination. All samples obtained from affected brain areas of patients AD3 and AD5 were PCR-negative for C. pneumoniae, and microscopic examination indicated that these 2 brains exhibited less severe neuropathology than did all other AD brains studied. Thus, PCR screening analysis indicated that DNA from C. pneumoniae was common in areas of the AD brain exhibiting disease-related neuropathology, but the DNA was uncommon in unaffected or less affected areas. The PCR screening assay also established that the C. pneumoniae DNA sequences which were detected were extremely rare in congruent brain regions from non-AD patients of similar age to the AD patients tested Apolipoprotein E genotypes were determined for all control and AD patients as described in Hixson et al. (1990, *J. Lipid Res.* 31:545–548), and the results are presented in Tables 1 and 2. This analysis indicated that 11 out of 19 AD patients (58%) had at least one copy of the ∈4 allele, and 2 patients were homozygous for the allele. The ∈4 allele was present in 4 out of 19 control patients (21%). Thus, the presence of the ∈4 allele correlated with AD in the patient population which was examined in this study.

TABLE 1

Summary of Control Patient Characteristics and Chlamydia-directed PCR Results

| Patient | Sex | Age at Death | Cause of Death[2] | Time PM[3] (hr) | PCR[1] CB | HP | Tcx[4] | Other | APOE[5] |
|---------|-----|--------------|-------------------|-----------------|-----------|-----|--------|-------|---------|
| C1 | f | 74 | respiratory failure | 14 | – | – | – | Pcx+ | ∈3/∈3 |
| C2 | f | 58 | multi-organ failure | 4 | – | – | – | | ∈3/∈3 |
| C3 | f | 90 | myocardial infarction | 9 | – | na | – | | ∈3/∈3 |
| C4 | m | 57 | cardiac arrest | 11 | – | – | – | | ∈3/∈4 |

TABLE 1-continued

Summary of Control Patient Characteristics and Chlamydia-directed PCR Results

| Patient | Sex | Age at Death | Cause of Death[2] | Time PM[3] (hr) | CB | HP | PCR[1] Tcx[4] | Other | APOE[5] |
|---|---|---|---|---|---|---|---|---|---|
| C5 | m | 66 | sepsis | 8 | – | – | – | | ε3/ε4 |
| C6 | f | 78 | pulmonary disease | 5 | – | na | – | | ε3/ε3 |
| C7 | f | 83 | renal failure | 3 | – | na | – | | ε3/ε3 |
| C8 | m | 71 | aortic aneurism | 6 | – | na | – | | ε3/ε3 |
| C9 | f | 81 | respiratory failure | 8 | – | na | – | | ε3/ε3 |
| C10 | m | 50 | adenocarcinoma | 10 | – | na | – | | ε3/ε3 |
| C11 | m | 68 | adenocarcinoma | 4 | – | na | – | | ε3/ε4 |
| C12 | f | 90 | lacunar infarcts | 4 | – | na | – | | ε3/ε4 |
| C13 | f | 84 | pneumonia | 7 | – | na | – | | ε3/ε3 |
| C14 | m | 64 | respiratory failure | 10 | – | na | na | Pfcx– | ε2/ε3 |
| C15 | m | 74 | respiratory failure | 5 | – | na | na | Pfcx– | ε3/ε3 |
| C16 | m | 77 | congestive heart failure | 5 | – | na | na | Pfcx– | ε3/ε3 |
| C17MS[6] | m | 71 | na | 17 | – | – | – | | ε2/ε3 |
| C18MS | f | 74 | sepsis | 7 | – | – | – | | ε3/ε3 |
| C19MS | m | 69 | cancer | 3 | – | – | – | | ε3/ε3 |

[1]Independent PCR assays targeting the 16S rRNA and omp1 genes of *C. pneumoniae* from each patient. All samples were negative in both assays except for the Pcx sample for patient C1, which was weakly PCR-positive. The positive result in the Pcx sample of patient C1 was confirmed using nested RT-PCR amplification of RNA corresponding to hsp72 and the KDO transferase genes. A fully consistent set of samples was not available for the PCR and other analyses described for most patients studied here.
[2]Proximal cause of death, given as listed on autopsy report.
[3]PM, post-mortem.
[4]CB, cerebellum; HP, hippocampus; TCx, temporal cortex; PCx, parietal cortex; Pfcx, prefrontal cortex; na, not available.
[5]APOE genotype was determined as described in Hixson et al., 1990, J. Lipid Res., 31:545–548.
[6]Patients indicated as MS had multiple sclerosis.

TABLE 2

Summary of AD Patient Characteristics and Chlamydia-directed PCR Results

| Patient | Sex | Age at Death | Cause of Death[2] | Time PM[3] (hr) | CB | HP | PCR[1] Tcx[4] | Other | APOE[5] |
|---|---|---|---|---|---|---|---|---|---|
| AD1 | f | 82 | cardiac arrest | 11 | – | + | na | | ε3/ε3 |
| AD2 | f | 85 | cardiac arrest | 7 | – | + | na | | ε3/ε4 |
| AD3 | f | 81 | cancer | 10 | – | – | na | | ε3/ε3 |
| AD4 | m | 87 | cardiac arrest | 6 | – | + | na | | ε3/ε3 |
| AD5 | f | 77 | cancer | 15 | – | – | na | | ε3/ε3 |
| AD6 | m | 68 | sepsis | 7 | – | + | + | Pcx+ | ε3/ε3 |
| AD7 | f | 82 | cardiac arrest | 12 | – | + | na | | ε3/ε4 |
| AD8 | f | 61 | lung carcinoma | 23 | – | na | + | Fcx+ | ε4/ε4 |
| AD9 | f | 78 | pneumonia | 22 | + | na | + | | ε2/ε4 |
| AD10 | f | 86 | heart failure | 11 | + | na | + | | ε3/ε4 |
| AD11 | f | 70 | gangrenous bowel | 9 | – | na | + | Pcx+ | ε3/ε4 |
| AD12 | f | 79 | sepsis | 16 | – | na | + | | ε3/ε3 |
| AD13 | f | 70 | aspiration pneumonia | 24 | – | na | + | | ε4/ε4 |
| AD14 | f | 87 | pneumonia | 8 | – | + | + | | ε3/ε3 |
| AD15 | f | 90 | atherosclerosis | 9 | – | na | + | | ε3/ε4 |
| AD16 | m | 67 | systemic infection | 8 | + | na | na | Pfcx+ | ε3/ε4 |
| AD17 | f | 78 | respiratory failure | 6 | – | na | na | Pfcx+ | ε3/ε3 |
| AD18 | f | 74 | pneumonia | 3 | – | na | na | Pfcx+ | ε3/ε4 |
| AD19 | f | 78 | renal failure | 4 | + | na | na | Pfcx+ | ε3/ε3 |

[1]Independent PCR assays targeting the 16S rRNA and omp1 genes of *C. pneumoniae* from each patient. All samples indicated as positive were unequivocally positive in both assays.
[2]Proximal cause of death, given as listed on autopsy report.
[3]PM, post-mortem.
[4]CB, cerebellum; HP, hippocampus; TCx, temporal cortex; PCx, parietal cortex; Fcx, frontal cortex; Pfcx, prefrontal cortex.
[5]APOE genotype was determined by the method of Hixson et al., 1990, J. Lipid Res., 31:545–548.

Ultrastructural Localization of *C. pneumoniae* in the Brain of Alzheimer's Disease Patients.

To confirm the PCR screening results and to identify the organism in affected CNS regions, brain sections obtained from AD patients and non-AD patients were analyzed using electron microscopy (EM) and immunoelectron microscopy (IEM). Brain tissues obtained from AD and non-AD patients were immersion-fixed in 4% para-formaldehyde in PBS and cut into 1 mm³ blocks. Blocks were osmicated in 1% $OsO_4$ prior to propylene oxide/resin infiltration and embedment in Embed-812 (Electron Microscopy Sciences, Fort Washington Pa.). Sections were cut on a Sorvall Porter-Bloom MT2B ultramicrotome, post-stained with 2% uranyl acetate, and viewed and photographed on a Zeiss 10 electron microscope.

In all species of *Chlamydia*, the extracellular, infectious form of the organism denoted the elementary body (EB) alternates with the intracellular, vegetative growth form denoted the reticulate body (RB) (Stephens, 1994, In: *Chlamydial Infections*; J. Orfila et al., eds., Societa Editrice Esculapio, Bologna, Italy, p. 377–386). Electron microscopic analysis of a survey of tissue sections revealed that areas of the hippocampus, temporal cortex, and/or other regions of AD brains exhibiting neuropathology also contained structures whose morphology was consistent with that of EB and RB forms of *C. pneumoniae* (FIG. 1) (Miyashita et al., 1993, *J. Med. Microbiol.* 38:418–425 ). These structures were localized in variable-sized inclusions within cells in the neuropil (e.g., FIG. 1, Panel A, B, and E). Often, a distinct membrane with internal electron-dense material could be distinguished, and the pear-shaped EB morphology typical of some *C. pneumoniae* strains was seen (FIG. 1, Panel B) (Miyashita et al., supra). Structures resembling RB in the process of cell division were frequently identified. The sizes of the chlamydia-like bodies observed ranged from 0.2–1.0 µm in diameter, which is the range characteristic for typical *C. pneumoniae* EB and RB (Miyashita et al., supra). The data in FIG. 1 are representative of the 10 AD brains subjected to EM analysis; no similar objects were found in identical analyses of tissues from 6 control patients, except in sections obtained from parietal cortex of patient C1. Thus, ultrastructural studies of areas of AD brains exhibiting neuropathology, but not congruent areas from control brains, revealed forms consistent in size and morphology with those typical of *C. pneumoniae*.

To confirm that the chlamydia-like bodies observed were *C. pneumoniae*, IEM studies were conducted to examine PCR-positive brains previously analyzed by EM. These studies were conducted with a highly-specific primary monoclonal antibody which targets an as yet unidentified outer membrane protein (OMP) of *C. pneumoniae* (clone RR402 (Poulakkainen et al., 1995, *Microbiol. Immunol.* 39:551–554); Washington Research Foundation, Seattle Wash.). Binding of the primary antibody was visualized via a gold-conjugated secondary antibody. For pre-embed IEM, 1 mm³ blocks of tissue were fixed overnight in 0.05% glutaraldehyde and 0.1% saponin in 0.2 M phosphate buffer at pH 7.0. After fixing, tissues were blocked for 2 hr in 100 mM ammonium chloride in 0.2 M phosphate buffer at pH 7.0. The tissues were then incubated with an anti-OMP monoclonal antibody diluted 1:10 in 0.2 M phosphate buffer at pH 7.0 which contained 5% cold water fish gelatin (CWFG; Sigma Chemical Co., St. Louis Mo.). Following rinses in 0.2 M phosphate buffer containing 5% CWFG and 20 mM glycine, tissues were incubated overnight at 4° C. with 15 nm gold-conjugated anti-mouse secondary antibody (Amersham Life Sciences, Arlington Heights Ill.) diluted 1:50 in 0.2 M phosphate buffer. Subsequently, tissues were rinsed in 0.2 M phosphate buffer and refixed in 2% glutaraldehyde solution, followed by immersion in 1% $OsO_4$ for 30 min at room temperature. Tissues were dehydrated in ethanol, contrast enhanced with 2% uranyl acetate, and processed for embedment in epon resin. Thin sections were prepared, viewed, and photographed as above. For post-embed IEM, thin sections of tissues embedded in Epon 812 were etched with 7% $H_2O_2$ for 60–75 sec and rinsed with water. Sections were treated with citric acid buffer at pH 6 for 2 min, rinsed with water, and incubated for 1 hr with a primary anti-OMP monoclonal antibody (undiluted; also clone RR402 obtained from Dako Corp., Carpenteria Calif.). Sections were rinsed in water, blocked for 2 min with 1% CWFG in PBS containing 0.1% acetylated-BSA. Sections were incubated with 15 nm gold-conjugated mouse secondary antibody (Amersham) diluted 1:5. Sections were then rinsed, post-stained with 2% uranyl acetate, and viewed. Background labeling was extremely low, and no significant or specific labeling was observed in sections obtained from 7 PCR-negative non AD patients.

Results of the IEM analysis representative of the 10 PCR-positive AD patients analyzed are included in FIG. 1. The anti-OMP monoclonal antibody labeled the EB form (FIG. 1, Panel C) and the RB form (FIG. 1, Panel D), confirming the presence of both developmental forms in the AD brain. Organisms exhibited variable distribution of immunoreactivity including partial and complete circumferential labeling, and immunolabeled bacteria were observed often in sections displaying neurodegenerative changes typical of AD (see below). The only normal component observed in tissue sections which resembled the objects in FIG. 1 were lysosomal dense bodies within dystrophic neurites. However, these lysosomal dense bodies were never labeled with the anti-OMP monoclonal antibody. Thus, IEM analysis of affected brain regions of AD patients confirmed that *C. pneumoniae* was present in those tissues and that these bacteria were absent in tissues from congruent brain regions of non-AD patients.

Immunohistochemical Localization of *C. pneumoniae* in the Alzheimer's Brain.

Immunohistochemical analysis of tissues from affected regions of AD brains and congruent regions from non-AD control brains was performed to identify specific area(s) and host cell types within which the bacterium resides. These analyses employed two monoclonal antibodies. The first antibody was a genus specific monoclonal antibody targeting the lipopolysaccharide (LPS) of *Chlamydia*, and the second antibody was the OMP specific monoclonal antibody employed in IEM studies.

Formalin-fixed paraffin-embedded blocks of tissue were cut into 7–10 µm sections and prepared for immunohistochemical analysis as described in Appelt et al., supra. Briefly, after standard rehydration and antigen retrieval, tissues were quenched for endogenous peroxidase before blocking for non-specific binding by incubation for 1 hour with 5% dried milk solids in Tris buffer, also containing 1% cold water fish gelatin. Sections from the formalin-fixed tissues were incubated with the primary monoclonal antibody targeting an OMP of *C. pneumoniae* (Washington Research Foundation; 1:50–1:250 dilution) or with the commercial, identical monoclonal antibody from the Dako Corp. (1:5 dilution in 5% dried milk solids). In related studies, a monoclonal antibody targeting the chlamydial LPS protein (Chiron Diagnostics) was used at a 1:50–1:250 dilution in 5% dried milk solids. Slides were incubated with the primary antibody for 1–4 hours at 4° C., washed with Tris buffer at room temperature, and then incubated with a 1:200 dilution of a goat anti-mouse secondary antibody (Amersham) in 5% dried milk solids for a minimum of 1 hour at room temperature or overnight at 4° C. After rinsing, tissues were incubated with ClonoPAP (mouse; Stemberger Inc., Baltimore Md.; 1:200 dilution in 5% dried milk solids) for 30 minutes. Slides were washed in Tris buffer before and after development with 0.05% DAB (Sigma Chemical Co., St. Louis Mo.) in 0.01% $H_2O_2$ for 8 min at room temperature. Tissues were dehydrated with ethanols/xylenes and mounted in permount. Sections were examined using an Olympus BX60 microscope with epifluorescence.

Figure 2:
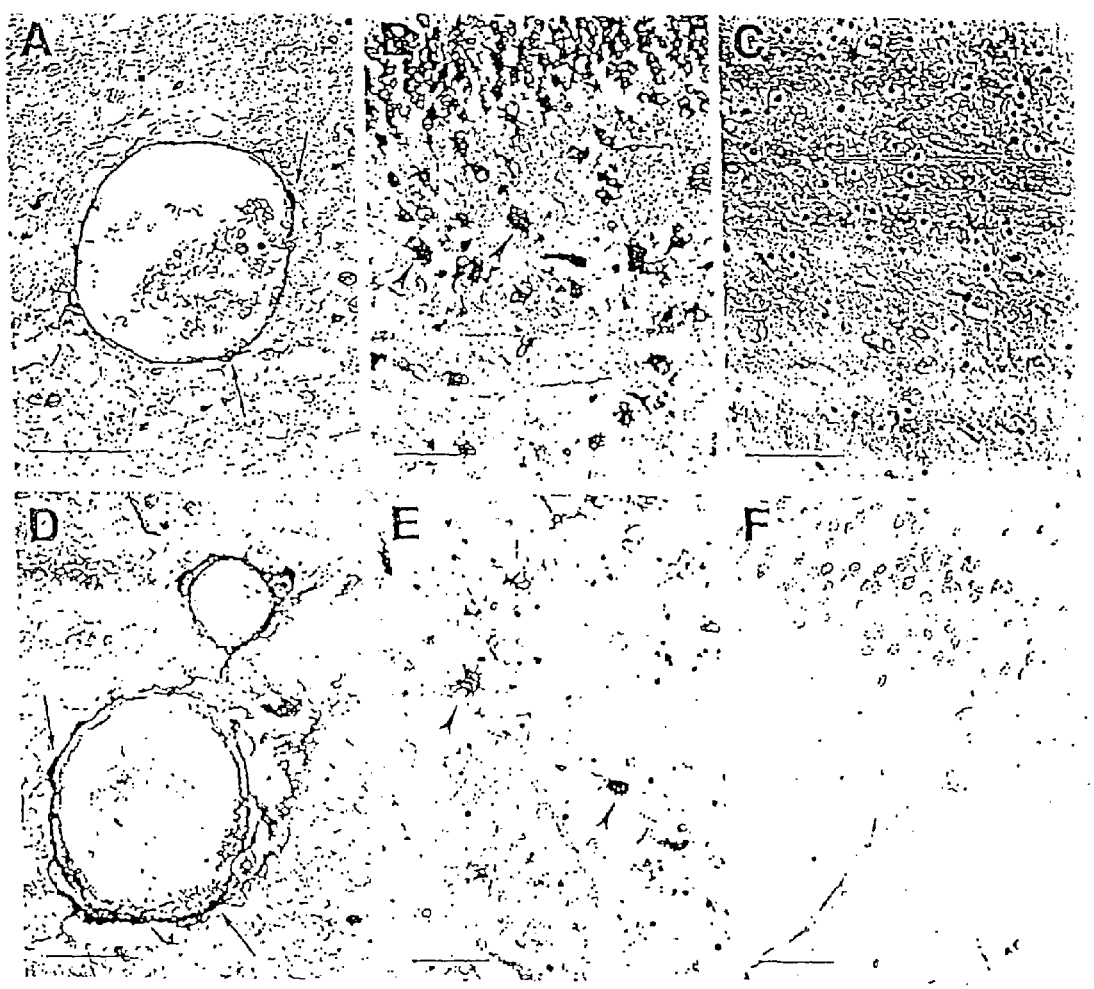
FIG. 2 is a series of images depicting immunohistochemical analysis of brain tissues obtained from control non-AD patients and AD patients using either a primary monoclonal antibody that is specific for *C. pneumoniae* outer membrane protein (anti-OMP) or a genus-specific primary monoclonal antibody that is specific for a lipopolysaccharide (LPS) of chlamydia (anti-LPS). Panel A depicts anti-LPS immunolabeling of perivascular cells (small arrows) in the temporal cortex tissue of patient AD4 (bar=50 µm). Panel B depicts anti-LPS immunolabeling of apparent glial cells (large arrow heads) in the dentate gyrus tissue of patient AD4 (bar=50 µm). Panel C depicts anti-LPS immunolabeling of temporal cortex tissue obtained from a control non-AD patient (C17MS, Table 1) (bar=50 µm). Panel D depicts anti-OMP immunolabeling of perivascular cells (small arrows) in the temporal cortex tissue of patient AD2 (bar=25 µm). Panel E depicts anti-OMP immunolabeling of apparent glial cells (large arrow heads) in the temporal cortex tissue of patient AD7 (bar=50 µm). Panel F depicts anti-OMP immunolabeling of tissue from the dentate gyrus tissue of a control non-AD patient (C18MS, Table 1) (bar=1.0 µm).

In sections of hippocampus and temporal cortex from AD brains, a consistent pattern of immunolabelling was observed in perivascular regions of small-/medium-sized blood vessels in the neuropil (FIG. 2, Panels A and D). In most sections, specific labeling also appeared in microglia- and astroglia-like cells (FIG. 2, Panels B and E). In congruent sections obtained from brains of the 6 non-AD patients examined, no immunolabelling was observed using either the anti-LPS or anti-OMP monoclonal antibody (FIG. 2, Panel C and F). Similar brain sections obtained from the 2 AD patients that were negative for the presence of *C. pneumoniae* DNA were also examined and both were immunonegative for *C. pneumoniae* even though they exhibited mild AD-related neuropathology Staining of AD brain sections sometimes revealed cellular processes, presumably from pericytes (see below), enclosing/abutting the abluminal surface of blood vessels. The pattern of immunoreactivity was consistent in the 10 AD brains examined, though there was some variability in the level of immunopositivity. This variability probably reflects a difference in bacterial load in the tissues examined but also may indicate sampling irregularity. Thus, immunohistochemical analysis confirmed the presence of *C. pneumoniae* in affected AD brain regions and localized the bacterium to non-neuronal cells.

Figure 3:
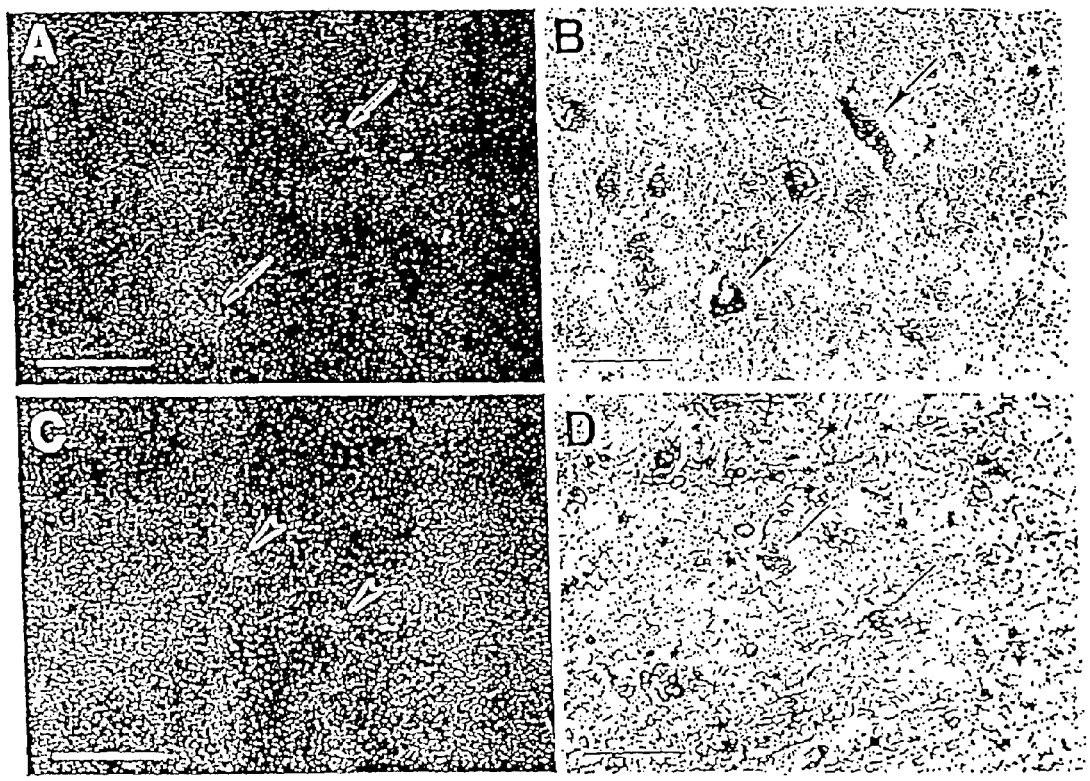
FIG. 3 is a series of images depicting immunohistochemical analysis of brain tissues obtained from AD patients using double immunolabeling with a primary monoclonal antibody that is specific for *C. pneumoniae* outer membrane protein (anti-OMP) and a cell specific primary antibody. Panels A and B depict temporal cortex tissue sections obtained from patient AD4 which were double immunolabeled with a chlamydial anti-LPS monoclonal antibody (Panel A, small arrows) and an anti-glial fibrillary acidic protein monoclonal antibody (Panel B, large arrows). Panels C and D depict temporal cortex tissue sections obtained from patient AD4 which were double immunolabeled with a chlamydial anti-OMP antibody (Panel D, arrows) and with an anti-inducible nitric oxide synthase polyclonal antibody (Panel C, arrowheads). Labeled cells in Panels A and C were illuminated using an FITC-conjugated secondary antibody, while those in Panels B and D were identified by DAB development. (Bars=50 µm).

Identification of the Host Cells in the Brain of an Alzheimer's Disease Patient which are Infected with *C. pneumoniae*: Relationship of the Host Cells to Neuropathology Double immunolabelling was employed to identify the *Chlamydia*-bearing cell types observed above, and to define the relationship between infected cells and NFT and NSP. Double immunolabelling was accomplished essentially as described above. Double immunolabelling of tissue sections from several AD brains using a polyclonal anti-chlamydial LPS antibody and a monoclonal anti-glial fibrillary acidic protein (GFAP) antibody (Miyashita et al., supra) demonstrated that astroglial cells were a common host for *C. pneumoniae* in the AD brain. FIG. 3 presents representative double immunolabelling results for the 12 AD patients analyzed. Cells identified by the anti-LPS polyclonal antibody (FIG. 3, Panel A) co-localized with cells expressing GFAP (FIG. 3, Panel B). Double immunolabelling of tissue sections was also done using a polyclonal antibody specific for inducible nitric oxide synthase (iNOS), an enzyme produced by activated microglia (Merrill et al., 1993, *J. Immunol.* 151:2132–2141), and an anti-OMP antibody specific for *C. pneumoniae*. Cells identified by the anti-iNOS antibody (Transduction Laboratories, Lexington Ky.) (FIG. 3, Panel C) colocalized with cells labeled with the anti-OMP antibody (FIG. 3, Panel D). Thus, infected host cells include astroglia and activated microglia. The *Chlamydia*-infected cells surrounding blood vessels in the AD brain are probably pericytes, as indicated by data in FIG. 2, Panels A and D. Although no single surface protein uniquely characterizes pericytes, the anti-iNOS polyclonal antibody was used in combination with the anti-OMP monoclonal antibody to identify this cell type, since expression of this enzyme is induced in infected pericytes (Chakravarthy et al., 1995, *Curr. Eye Res.* 14:285–294). These data indicate that at least three cell types, astroglia, microglia, and pericytes, harbor *C. pneumoniae* in the AD brain.

Figure 4:
FIG. 4 is a series of immunohistochemical images of consecutive tissue sections obtained from the temporal cortex of patient AD7 depicting immunoreactivity for *C. pneumoniae* in areas of neuropathology in the AD brain. In Panel A, neuritic pathology characteristic of AD was demonstrated by immunolabeling with an anti-PHF-1 monoclonal antibody (large arrows). In Panel B, using consecutive tissue sections from the same sample, immunolabeled glial cells (small arrows) infected with *C. pneumoniae* (small arrows) are shown using the anti-OMP monoclonal antibody. Bars=25 µm.

The PHF-1 monoclonal antibody is used to identify neuritic pathology in the AD brain (Greenberg, 1990, *Proc. Natl. Acad. Sci. USA* 87:5827–5831). FIG. 4 presents typical consecutive tissue sections obtained from temporal cortex of an AD patient labeled with the PHF-1 (FIG. 4, Panel A) and anti-OMP (FIG. 4, Panel B) antibodies. Staining with the latter demonstrated the common presence of *Chlamydia*-infected glial cells near PHF-tau protein deposition in neurites within NSP in the 8 AD patients so analyzed. For the same patients, similar labeling of brain areas with few or no NSP demonstrated that virtually no cells harboring *C. pneumoniae* were present; in sections from 7 non-AD brains, no infected cells were identified. Thus, *Chlamydia*-infected astroglia and microglia in the AD brain were concentrated primarily in regions of neuropathology.

Transcriptional Activity of *C. pneumoniae* in the Alzheimer's Brain.

Recent work has indicated that in some cases, RNA can remain intact in brain tissues for several hours post-mortem (Itzhaki et al., supra; Kingsbury et al., 1995, *Mol. Brain Res.* 28:311–318). To determine whether *C. pneumoniae* is transcriptionally active during CNS infection of AD patients, reverse transcription-polymerase chain reaction (RT-PCR) assays targeting two mRNAs from *C. pneumoniae* were performed. The two targeted mRNAs were that specifying the KDO transferase enzyme, which is required for bacterial LPS synthesis, and that specifying the Mr=72000 heat shock protein (hsp72).

RNA was prepared from the hippocampus and/or temporal cortex of patients AD2 and AD 14, and from the cerebellum of these patients. Nucleic acids were prepared from tissue samples as described in Branigan et al., 1996, *Arthritis Rheumat.* 39:1740–1746, and RNA was prepared from total nucleic acids by digestion with RNase-free DNase1 (RQ1; Promega Biotech, Madison, Wis.). Purity of the RNA was assessed by PCR without reverse transcription, using the primers described below. One picogram of total RNA was RT-PCR amplified as described in Montarras et al., 1994, In: *The Polymerase Chain Reaction*, Mullis et al., eds., Birkhäuser Press, Boston, Mass., pp. 277–294. Nested primer systems were employed to detect both the *C. pneumoniae* hsp72 gene (outer: bases 160–184, 1066–1086; inner: bases 373–392, 799–822 (Perez-Melgosa et al., 1994, *Infect. Immun.* 62:880–886) and the KDO transferase gene (outer: bases 132–152, 946–965; inner: bases 527–549, 797–815 (Lebau et al., 1994, *Mol. Microbiol.* 18:391–399). These primers were analyzed for sequence specificity via "Blast" comparison with all DNA sequences in the GenBank and were tested extensively for sequence specificity for the relevant genes. DNA fragment sizes of 450 bp and 289 bp indicated positive signals for the hsp72 and KDO transferase mRNAs, respectively. The identity of PCR and RT-PCR products was confirmed by hybridization.

Figure 5:
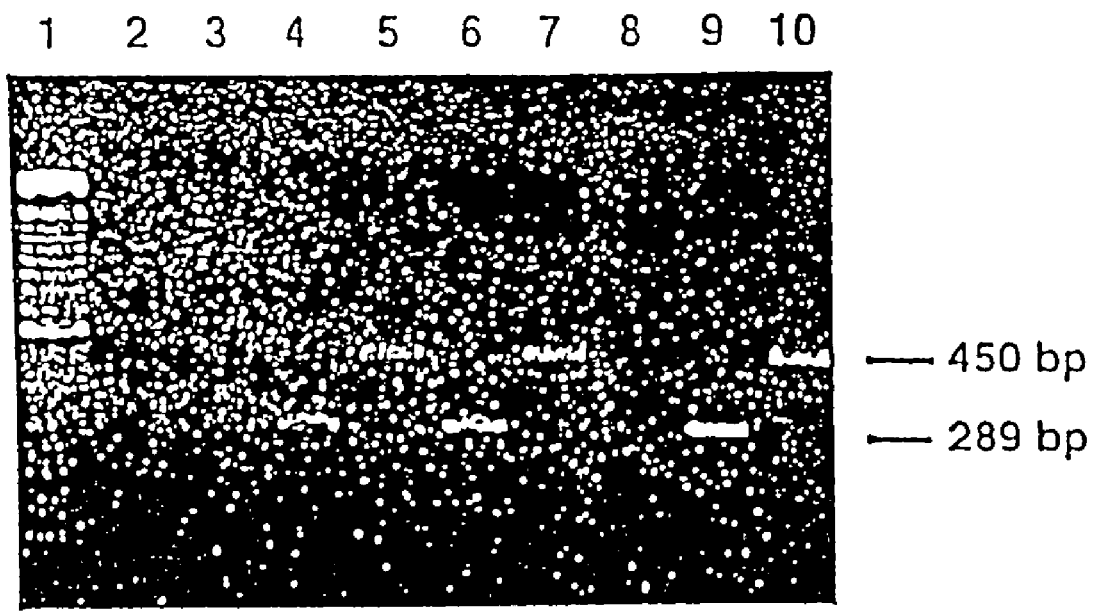
FIG. 5 is an image of an ethidium bromide stained gel depicting RT-PCR analysis of total RNA obtained from two AD patients, using primers targeting the KDO transferase and the hsp72 mRNAs of *C. pneumoniae*. The lanes are as follows: (1) 100 bp size standards; (2) analysis of cerebellum RNA obtained from patient AD2 for KDO transferase mRNA; (3) analysis of cerebellum RNA obtained from patient AD14 for KDO transferase mRNA; (4) analysis of hippocampus RNA obtained from patient AD2 for KDO transferase mRNA; (5) analysis of hippocampus RNA obtained from patient AD2 for hsp72 rRNA; (6) analysis of hippocampus RNA obtained from patient AD14 for KDO transferase mRNA; (7) analysis of hippocampus RNA obtained from patient AD14 for hsp72 mRNA; (8) a negative control amplification using the KDO transferase primers and water substituted for the template nucleic acids; (9) a positive control for KDO transferase amplification using *C. pneumoniae* genomic DNA as a template; (10) a positive control for hsp72 amplification using *C. pneumoniae* genomic DNA as a template.

As exemplified in FIG. 5, the results demonstrated that RNA from the hippocampus of both the AD2 and the AD14 patient contained both bacterial transcripts and that RNA from the temporal cortex of patient 14 also contained both transcripts. In contrast, RNA prepared from the cerebellum of the two patients AD2 and AD14 was negative for both messenger RNAs. These results confirmed the negative result obtained during PCR analysis of *C. pneumoniae* DNA in the cerebellum of these two patients (Table 2). Thus, *C.* pneumoniae genes are expressed during CNS infection of AD patients, suggesting that infection by this organism involves vegetatively-growing bacteria.

Figure 6:
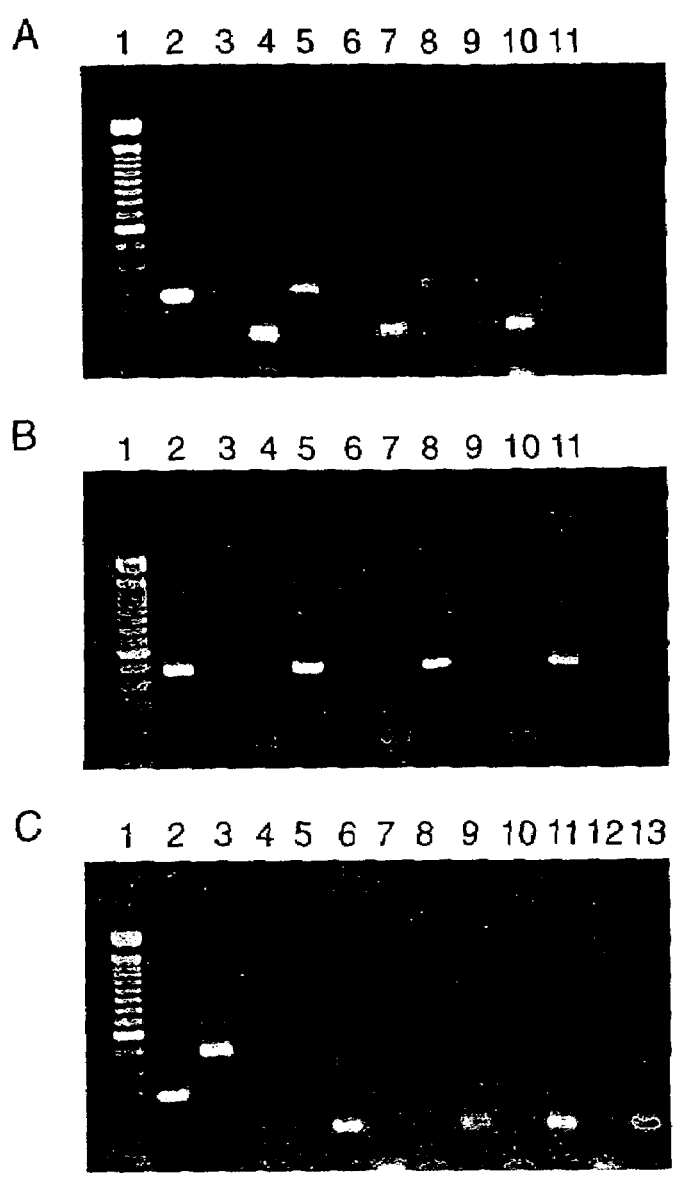
FIG. 6 is a series of images of control and patient-directed RT-PCR analyses of total RNA prepared from two AD and two control patients, using primers targeting mRNAs specific for the *C. pneumoniae* KDO transferase gene and the gene specifying a Mr=76000 protein. The quality of RNA preparations was examined in RT-PCR reactions targeting the human host cell mRNA specifying subunit 4 of cytochrome oxidase (COIV). RNA was prepared, and reactions performed and the results were visualized, as described herein. Panel A: Analyses targeting the *C. pneumoniae* KDO transferase mRNA. Lanes are: 1, 100 bp size standards; control PCR analysis for the KDO gene itself using 2, purified *C. pneumoniae* DNA and 3, purified DNA obtained from astrocytoma (SW1088) cells in culture; 4, control PCR analysis targeting the COIV sequence in purified DNA obtained from cultured SW1088 cells; 5, control PCR analysis targeting the KDO transferase sequence in purified DNA obtained from *C. pneumoniae* (TW-183)-infected SW1088 cells; RT-PCR analysis targeting the chlamydial KDO transferase mRNA in total RNA obtained from the hippocampus of patient AD2, 6, without reverse transcription and 8, with reverse transcription prior to amplification; 7, RT-PCR targeting host COIV mRNA in RNA obtained from the hippocampus of patient AD2; RT-PCR analysis targeting the chlamydial KDO transferase mRNA in total RNA obtained from the hippocampus of patient AD 14, 9, without reverse transcription and 11, with reverse transcription prior to amplification; 10, RT-PCR targeting host COIV mRNA in RNA obtained from hippocampus of patient AD2. Panel B: Analyses targeting the *C. pneumoniae* Mr=76000 protein mRNA. Lanes are: 1, 100 bp size standards; control PCR analysis for the Mr=76000 gene using 2, purified *C. pneumoniae* DNA and 3, purified DNA obtained from astrocytoma (SW1088) cells in culture; 4, control PCR analysis targeting the COIV sequence in purified DNA obtained from cultured SW1088 cells; 5, control PCR analysis targeting the Mr=76000 protein gene in purified DNA obtained from *C. pneumoniae* (TW-183)-infected SW1088 cells; RT-PCR analysis targeting the chlamydial Mr=76000 mRNA in total RNA obtained from the hippocampus of patient AD2, 6, without reverse transcription and 8, with reverse transcription prior to amplification; 7, RT-PCR targeting host COIV mRNA in RNA obtained from the hippocampus of patient AD2; RT-PCR analysis targeting the chlamydial Mr=76000 mRNA in total RNA obtained from the hippocampus of patient AD 14, 9, without reverse transcription and 11, with reverse transcription prior to amplification; 10, RT-PCR targeting host COIV mRNA in RNA obtained from the hippocampus of patient AD14. Panel C: Control and patient-directed RT-PCR analyses of total RNA prepared from two control patients and from PCR-negative regions of the two AD patients. Lanes are: 1, 100 bp size standards; PCR analyses targeting sequences in 2, the KDO transferase gene and 3, the Mr=76000 protein gene both using purified DNA obtained from *C. pneumoniae* (TW-183)-infected SW1088 cells in culture; RT-PCR analysis targeting the chlamydial KDO transferase mRNA using total RNA obtained from the hippocampus of control patient C4, 4, without reverse transcription and 5, with reverse transcription prior to amplification; 6, RT-PCR targeting host COIV mRNA in RNA obtained from the hippocampus of patient C4; RT-PCR analysis targeting the Mr=76000 MRNA using total RNA obtained from the hippocampus of control patient C2, 7, without reverse transcription and 8, with reverse transcription prior to amplification; 9, RT-PCR targeting host COIV mRNA in RNA obtained from the hippocampus of patient C2; 10, KDO transferase mRNA-directed RT-PCR using total RNA obtained from the cerebellum of patient AD2; 11, RT-PCR for host COIV mRNA using RNA obtained from the cerebellum of patient AD2; 12, Mr=76000 mRNA-directed RT-PCR using total RNA obtained from the cerebellum of patient AD14; 13, RT-PCR for host COIV mRNA using RNA obtained from the cerebellum of patient AD14.

Additional RT-PCR experiments were performed as follows. RNA was prepared from total nucleic acids by digestion with RNase-free DNase 1 (RQ1; Promega Biotech, Madison Wis., USA); purity was assessed by PCR using primers below, without reverse transcription. RT reactions used 1 μg total RNA, were done as described (Montarras et al., 1994, In: Mullis K. B., Ferre F., Gibbs F. A. (eds) The Polymerase Chain Reaction. Birkhäuser Press, Boston, pp 277–294), and employed nested primer systems for the gene specifying a Mr=76000 protein containing an epitope specific for *C. pneumoniae* (outer: bases 160–184, 1066–1086; inner: bases 373–392, 799–822; (Perez-Melgosa et al., 1994, Infect. Immun. 62:880–886)), and the KDO transferase gene from the organism (outer: bases 132–152, 946–965; inner: bases 527–549, 797–815; (Lobau et al., 1994, Mol. Microbiol. 18:391–399)). As an internal control for the quality of RNA analyzed, an RT-PCR assay targeting transcripts from the human nuclear gene specifying subunit 4 of cytochrome oxidase (COIV), the terminal complex in the mitochondrial electron transport chain (bases 184–213, 319–348; (Lomax et al., 1990, Gene 86:209–216)) was employed. Primers for the *C. pneumoniae* transcripts were designed and their specificity was confirmed as given above. Similar to the PCR screening assays, precautions taken in preparation of RNA to be analyzed and in the analyses themselves included independent preparation of RNA from separate portions of the same samples by different investigators in different laboratories and biological hoods, and use of several hoods and reserved sets of pipettors for preparation of reaction mixtures. Positive signals for the *C. pneumoniae* Mr=76000 protein and KDO transferase mRNAs were bands of 449 bp and 288 bp, respectively. Product size for the COIV mRNA was 164 bp. Identity of PCR and RT-PCR products was confirmed by hybridization. The results of these assays are presented in FIG. 6 as described below.

In these analyses, mRNAs transcribed from the *C. pneumoniae* gene encoding the KDO transferase enzyme, which gene is required for bacterial LPS synthesis, and mRNA transcribed from the gene specifying a Mr=76000 protein that includes a species-specific epitope of the organism, were targeted. As an internal control for the quality of RNA analyzed, an RT-PCR assay targeting the human nuclear gene COIV was employed. RNA was prepared from hippocampus or temporal cortex of patients AD2, AD14, C5, and C18MS, and these preparations were analyzed for the two *C. pneumoniae*, as well as the host COIV, mRNAs. The representative control assays given in FIG. 6, panels A–C demonstrate that neither of the *C. pneumoniae*-directed RT-PCR primer systems amplifies any sequences from human cells, and that the quality of RNA preparations analyzed was adequate for these studies. The experimental results presented in FIG. 6, panels A and B demonstrate that RNA obtained from brain regions exhibiting neuropathology in the two AD patients contained both of the targeted bacterial transcripts. In contrast, the assays shown in FIG. 6, panel C demonstrate that RNA prepared from congruent regions of two non-AD brains was negative for these bacterial mRNAs. RNA prepared from cerebellar tissue of patients AD2 and AD14, regions PCR-negative for *C. pneumoniae* DNA in these patients (FIG. 6, panel C; Table 2), was negative for each of the bacterial messengers. Thus, *C. pneumoniae* expressed at least some genes during CNS infection of AD patients, confirming that such infections involve metabolically-active, vegetatively-growing bacteria.

Correlation of High Titer Anti-*C. pneumoniae* IgG Antibodies with Alzheimer's Disease The presence and titers of anti-*C. pneumoniae* IgG antibodies was measured in a group of 12 non-demented, healthy control patients aged 70 years or older and in an equal number of living putative AD patients of the same ages. Antibody titer was measured in a standard ELISA assay using antibodies specific for *C. pneumoniae*, as described herein. In the control group, 84% of control patients were positive for the antibody, indicating that simple presence of anti-*C. pneumoniae* IgG in a given patient will not be useful in diagnosis. However, of the IgG positive controls, antibody titers in all but one were low, with a single individual possessing a titer suggestive of active/recent infection with the organism. Anti-*C. pneumoniae* IgG was present in 90% of putative AD patients, but titers in this group were significantly higher than those in control patients. Antibody titers in many of the putative AD patients suggested a current infection. Therefore, these results indicate that a determination of the serum titer of anti-*C. pneumoniae* antibodies can be used as a diagnostic tool for Alzheimer's disease.

Dissemination of *C. pneumoniae* to the Brain

The distribution and overall density of NSP, NFT, and NT can vary among the normally affected areas of the AD brain, and among individuals. However, one region which is universally affected in all AD patients is the hippocampus. The hippocampus has connections to the olfactory bulb, therefore indicating that one route of transmission of the bacterium to the brain is by passage of the organism from the nasal mucosa through the olfactory nerve tract to pathways leading to entorhinal cortex and hippocampus. Olfactory bulbs obtained from two AD patients were screened for the presence of *C. pneumoniae* DNA sequences using the primer systems for the 16S rRNA gene and the chlamydial major outer membrane protein (MOMP) gene (omp1) as described herein. Both bulbs contained high levels of *C. pneumoniae* DNA as assessed in both assays, indicating the presence of *C. pneumoniae* in the olfactory bulbs of these two AD patients. These results confirm that infection of the olfactory bulb is a likely route for passage of *C. pneumoniae* to the brain in patients having Alzheimer's disease. Given these data, it is possible to use solutions or sprays comprising anti-chlamydia compounds in order to neutralize or kill the organism prior to the development of symptoms caused by infection of the host with the organism.

Infection of Cultured Astrocytes with *C. pneumoniae*

A system of cultured astrocytoma cells infected with *C. pneumoniae* was developed to determine the effects of *C. pneumoniae* infection on the astrocytoma cells and to provide a test system for evaluating putative therapeutic compounds for Alzheimer's disease. An astrocytoma cell line (ATCC SWI088) was infected with the EB of *C. pneumoniae* (ATCC TW183). Several T25 flasks containing nearly confluent monolayers of astrocytoma cells were infected with approximately $10^8$ ifu of the bacteria. The term "ifu" (inclusion forming unit) is defined as infectious organisms as determined by the American Type Culture Collection from which pure cultures of *C. pneumoniae* were obtained for the present study. After 24 hours, infected and uninfected cultures were examined microscopically. The infected cultures exhibited cytoplasmic inclusions in approximately 80% of cells, whereas no evidence of inclusions was observed in uninfected cultures.

Infected and control cultures were then harvested and divided into two aliquots; one aliquot was fixed and the other was snap frozen at $-70°$ C. EM analysis of the fixed pellets revealed both developmental forms of the organism within cytoplasmic vesicles in host cells, and the identified forms were identical to those seen in brain tissue samples obtained from AD patients. RT-PCR analyses of RNA prepared from the frozen pellets of infected cells demonstrated the presence of *C. pneumoniae* KDO transferase and hsp72 specific mRNAs, neither of which were present in RNA prepared from EB or from uninfected astrocytoma cells. The presence of these transcripts and the evidence of visible inclusions indicate that EB were successfully taken up by the astrocytoma cells, and that EB to RB development took place within the inclusions.

Culture Analyses for *C. pneumoniae*

Culture analyses for *C. pneumoniae* were performed by infection of a human monocyte/macrophage cell line, THP-1 (ATCC Accession No. 45503, American Type Culture Collection, Rockville, Md.) (Kurosaka et al., 1998, J. Immunol. 161:6245–6249; Li et al., 1998, Cell Biol. Int. 22:13–20). Approximately 0.5 g of frozen brain tissue obtained from the temporal cortex of two patients previously determined to be *C. pneumoniae*-positive by PCR and immunohistochemical analyses, as well as congruent tissue samples obtained from two control brains, were subjected to three freeze-thaw cycles; tissues were homogenized and sonicated between cycles. From these samples, 100 µl of homogenate were mixed with $3\times10^6$ THP-1 cells in 2 ml 10% fetal calf serum in RPMI-1640, 0.5% HEPES buffer (pH 7.0). The homogenate and cells were centrifuged at 500×g for 30 minutes, diluted to 10 ml volume in medium, then cultured for 72 hour. Following this initial culture incubation, 1 ml of culture supernatant was used for a second passage on $3\times10^6$ fresh THP-1 cells; remaining cells from the initial 72 hour incubation were separated from debris by centrifugation on Ficoll-Paque (Pharmacia-Biotech, Piscataway N.J., USA) gradients. Cells obtained from both first and second culture passages were subjected to immunocytochemical analyses to confirm infection of the cultured THP-1 cells. Cells for immunocytochemistry were diluted to $2.5\times10^5$/ml in Hanks balanced salt solution, and 0.2 ml were cytospun onto ProbeOn+ (Fisher Biotech) at 500×g for 5 minutes, using a Shandon Cytocentrifuge III. Cells were fixed for at least 1 hour at room temperature with Streck Tissue Fixative (S.T.F.™ Streck Laboratories Inc., Omaha Nebr.), followed by a rinse with 1× Automation buffer (Biømeda, Foster City Calif.). After endogenous peroxidase deactivation, immunocytochemistry was performed using the Biostain Super ABC Mouse/Rat kit (Biømeda, Foster City, Calif.) as described by the manufacturer. Anti-surface protein mAb specific for *C. pneumoniae* (DAKO. Carpinteria, Calif.) and the genus-specific anti-LPS mAb (DAKO, IMAGEN-*Chlamydia* Kit) were each diluted 1:10 in Ab Diluting buffer (Biømeda) and incubated for 30 minutes at 37° C., followed by nine rinses with Automation buffer (Biømeda). Similar incubations and washes were performed for the secondary anti-mouse biotinylated antibody and Avidin-Biotin Complex (ABC) reagents. After a 1 minute incubation with peroxidase enhancer, antibody binding was detected with the horse radish peroxidase chromagen Diaminobenzidine Cobalt (Biømeda) by 5–10 minutes incubation at room temperature. Slides were prepared with Crystal-Mount (Biømeda) for light microscopy. EM analyses were also performed on THP-1 cells infected with *C. pneumoniae* isolated from brain tissues. For such studies, cells were centrifuged at 500×g for 5 minutes in 1.5 ml microcentrifuge tubes and fixed in 4% paraformaldehyde, 0.1% glutaraldehyde overnight at 4° C., then embedded and processed for EM, as described herein. Cytospins for EM were fixed with 4% paraformaldehyde, 0.1% glutaraldehyde and subjected to the "pop-off" technique (Bretschneider et al., 1981, Am. J. Clin. Path. 76:450–453), then processed for EM.

Figure 7:
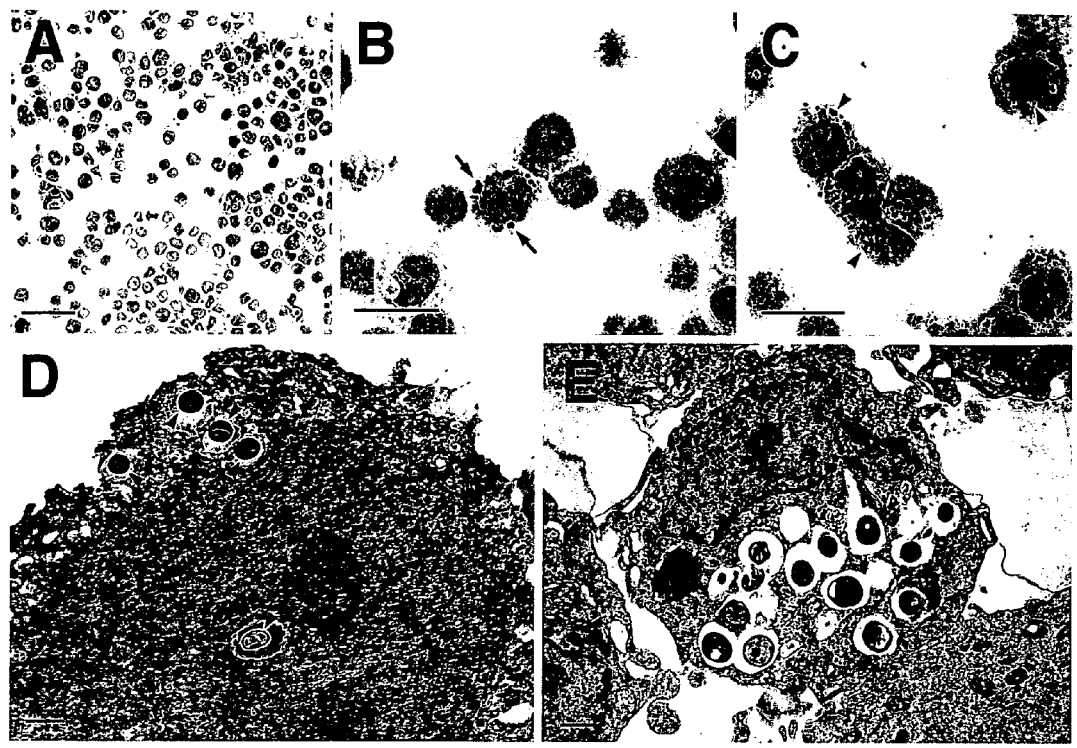
FIG. 7 is a series of images depicting immunocytochemical and electron microscopic analyses of *C. pneumoniae* infection in cultured THP-1 monocytic cells incubated with tissue homogenates of non-AD control and AD tissues. Panel A: THP-1 cells incubated with a tissue homogenate of temporal cortex from control brain C7 followed by immunolabelling with the anti-surface protein mAb for *C. pneumoniae* (bar=100 em). Panel B: THP-1 cells incubated for three days with tissue homogenate of temporal cortex from patient AD14. These cells were immunolabeled with the anti-surface protein mAb, which revealed cytoplasmic inclusions of *C. pneumoniae* (arrows) (bar=50 μm). Panel C: THP-1 cells incubated for seven days with tissue homogenate of hippocampus from patient AD7. Numerous inclusions of *C. pneumoniae* within these cells were immunolabelled with the anti-surface protein mAb (arrowheads) (bar=50 em). Panel D: EM analysis of a THP-1 cell infected with *C. pneumoniae* (arrowheads) following three days of culture with a tissue homogenate from temporal cortex of patient AD14 (bar=1.0 μm). Panel E: EM analysis of a THP-1 cell infected with *C. pneumoniae* following seven days of culture with a tissue homogenate from the hippocampus of patient AD7 (bar=1.0 μm).

Laboratory culture of an organism from a putative site of infection is considered to be the gold standard for demonstration that the organism is indeed present at that site. Thus, experiments were performed to culture *C. pneumoniae* from homogenates of two AD (AD7, AD14) and two control non-AD (C3, C7) brains, using the human monocyte cell line designated THP-1 as host. Previous studies have demonstrated that monocyte cell lines, such as THP-1, are susceptible to infection by the organism (Numazaki et al., 1995, J. Med. Microbiol. 42:191–195). Immunocytochemistry using the anti-surface protein and anti-LPS monoclonal antibody (mAb) was performed on cytospun THP-1 cells after culture with brain homogenates. THP-1 cells incubated with homogenates from temporal cortex of each control brain were completely negative for *C. pneumoniae* using either mAb for immunolabelling (e.g., FIG. 7, panel A). Host monocytes from cultures incubated with homogenates from temporal cortex of each AD patient, in contrast, displayed strong immunopositivity using both mAb after one passage (72 hour; FIG. 7, panel B) and after two passages (7 days; FIG. 7, panel C). Approximately 10% of cultured THP-1 cells were immunopositive for *C. pneumoniae* after 72 hours of culture, and ~70% were positive after the second passage. *C. pneumoniae* inclusions were also visualized within these infected host cells by EM, using duplicate cytospin preparations of homogenate-infected THP-1 cells as starting material; these studies demonstrated classic morphology of the organism after both first (FIG. 7, panel D) and second passages (FIG. 7, panel E; see Miyashita et al., 1993, J. Med. Microbiol. 38:418–425). Thus, infectious *C. pneumoniae* were present in autopsy brain tissues from the two AD patients subjected to culture analysis, but the organism was not present in congruent tissues from the two non-AD control patients studied.

EXAMPLE 2

In Situ Hybridization of *C. pneumoniae* in Alzheimer's Disease

In situ hybridization was utilized to further examine the association between *C. pneumoniae* and AD. Using a digoxigenin-labeled probe synthesized from the PCR product retrieved from previously analyzed AD brain tissues against the ompA gene of *Chlamydia pneumoniae*, it was possible to localize the *C. pneumoniae*-DNA sequence to the hippocampus, frontal cortex, and temporal cortex and not in the cerebellum of seven brains exhibiting neurodegeneration typical of AD. Within these areas, the probe appeared to immunolabel glial cells, pericytes, and blood vessels only in the areas with AD pathology. Neuronal labeling was not evident in the in situ positive areas. A novel technique, "in situ-Pop-off", demonstrated that the organisms within the in situ positive sections were ultrastructurally identical to the morphology of previously described *Chlamydia pneumoniae*. These data further confirm the localization of *C. pneumoniae* within areas of pathology in the Alzheimer brain, suggesting that the organism could play a significant role in the pathogenesis of this insidious disease.

Patient Samples

Postmortem tissue samples obtained from various brain regions of patients with and without AD were obtained from the Harvard Brain Tissue Resource Center and from the Allegheny University of the Health Sciences Department of Pathology and Laboratory Medicine. All samples from patients diagnosed as AD were confirmed at autopsy by histopathologic examination by a certified neuropathologist, using standard criteria (NINDS/CERAD). All AD patients were diagnosed clinically with late-onset disease. Samples from non-AD patients were age-matched to those of AD patients, and each set was examined histologically for NSPs and NFTs and confirmed as AD or non-AD.

Seven AD brains which had previously tested positive for *C. pneumoniae* (as described herein in Example 1) and three non-AD brains previously confirmed negative for the organism by equivalent techniques were examined. The mean age of death was 82 years old for the AD patients and 81 years old for the control population. Mean post-mortem intervals were 8 hours and 11 hours for AD and non-AD samples, respectively. The causes of death included cardiac arrest, cancer, gangrenous bowel, and pneumonia for the AD patients and acute bronchopneumonia, pneumonia, and sepsis for the non-AD control patients. The areas examined included the hippocampus, entorhinal cortex, temporal cortex, occipital cortex, and cerebellum in both AD and control samples.

Preparation of Nucleic Acids

Nucleic acids were prepared from tissue samples as described herein. DNA also was prepared from the monocyte cell line, THP-1, infected with *Chlamydia pneumoniae* extracted from infected Alzheimer's brains as described. One microgram of nucleic acid was used in each PCR assay. Elementary bodies of *C. pneumoniae* strain TW-183 were obtained from the American Type Culture Collection, and DNA was prepared from them for control amplifications. PCR assays for *C. pneumoniae* genomic DNA utilized a nested primer system, targeting an outer membrane protein gene, ompA, of *C. pneumoniae*. Primers, synthesized by Genosys US, were designed using GeneRunner® software (Hastings Software, Hastings N.Y.) and were derived from bases 26–43 and 567–548 (outer) and bases 115–135 and 462–444 (inner) of the *C. pneumoniae* ompA coding sequence. The primers were analyzed for sequence specificity via "Blast" comparison with all existing DNA sequences in the GenBank database. Cycling for PCR assays was done in a Perkin-Elmer 2400 thermocycler, and products were analyzed on 1.8% agarose gels. This assay produced a 350 bp product which was ligated into a M13 vector and sequenced on an automated sequencer ABI Prizm model 377 V3.0.

Using the TA cloning kit (Invitrogen, San Diego, Calif.), the remaining PCR product was ligated into the pCR 2.1 plasmid and INVαF' competent cells were transfected with this vector. The transfected cells were plated on LB-ampicillin treated agar plates and allowed to grow overnight at 37° C. White colonies were selected and grown overnight in LB-amp media. The extracted plasmid vector then was cut with the restriction endonuclease EcoRI prior to electrophoresing the DNA on a 1.8% agarose gel. Colonies which yielded a 350 bp band were grown in a MaxiPrep kit (Qiagen, Chatsworth, Calif.) for plasmid purification. The resulting nucleic acid pellet was resuspended in 10 mM Tris (pH 8.0) containing 1 mm EDTA. Quantitation of DNA yield was determined by two methods. Spectophotometric analysis resulted in a $OD_{260}/OD_{280}$ ratio of 2.0 and a concentration of 173 μg/ml of PCR-insert. Ethidium bromide fluorescent quantitation estimated to ~200 μg/ml for the band on the 1.8% agarose gel. The remaining plasmid was cut with EcoR1 endonuclease, excised from the gel using the Qiakit spin column system (Qiagen) and resuspended in $H_2O$ (pH 8.0) to a concentration of 73.3 ng/μl. The probes for in situ hybridization were generated by labeling the PCR product with deoxyuracil-bound-digoxigenin (DIG-dUTP) from the DIG-High Prime® kit (Boehringer-Mannheim, Indianapolis, Ind.) utilizing the random primed labeling technique. The yield of DIG-labeled probe was determined by comparison with a DIG-labeled control contained within the kit.

In Situ Hybridization

A modification of the protocol by Larsson, et al. was utilized for in situ hybridization analysis. Paraffin embedded tissues (5–9 μm) were deparaffinized in xylenes, rehydrated in graded ethanols, and washed twice for 5 min in 0.1 M PBS. Tissue sections were incubated in 0.1M glycine for 5 minutes, and 0.3% Triton X-100 for 15 minutes to reduce background. Slides were incubated for 30 minutes in proteinase K solution (10 μg/ml), post fixed for 5 minutes in 4% formaldehyde, and acetylated in 0.25% acetic anhydride for 10 minutes. Tissue sections were incubated for two hours in a humidified chamber at 37° C. with prehybridization solution containing 50% deionized formamide, 4×SSC, 1× Denhardt's solution, 500 μg/ml denatured salmon sperm DNA, 250 μg/ml yeast tRNA, and 10% dextran sulfate. After prehybridization, slides were incubated for 10 minutes at 65° C. in order to denature the genomic DNA and the probe, then overnight at 37° C. in a humidified chamber with hybridization solution (prehybridization solution containing 500 pg probe for each slide). Posthybridization washes were as follows: 2×SSC for 15 minutes at 42° C. (twice), 1×SSC for 15 minutes at 42° C. (once), 0.5×SSC for 15 minutes at 42° C. (twice) and 1× maleic acid buffer for 1 minutes at room temperature.

Immunodetection of the signal was carried out by incubation in 2× blocking solution (Boehringer-Mannheim) at room temperature followed by incubation with anti-digoxigenin alkaline phosphatase antibody (1:500)(Boehringer-Mannheim) in 2× blocking solution for four hours at 37° C. Slides were washed in maleic acid buffer and color detection buffer (Boehringer-Mannheim) for 10 minutes each, then incubated in freshly prepared NBT/BCIP in detection buffer (0.1M Tris-HCl, pH 9.5, 0.1M NaCl, 50 mM $MgCl_2$) overnight in a light-sealed humidified chamber. The reaction was stopped by washing slides in TE buffer, pH 8.0, then counterstained with nuclear-fast-red for 10 minutes at room temperature prior to a final wash in TE buffer. The slides were mounted in Gelmount® aqueous mounting media.

Electron-microscopic ("in situ-Pop-off") Analysis

Tissue sections obtained from AD and control brains were cut from areas typically demonstrating neuropathology (e.g. hippocampus, temporal cortex) and from areas usually spared of AD pathology (e.g. cerebellum). The tissue sections were processed through the previously described in situ hybridization protocol excluding mounting in Gelmount®. The slides were then immersed twice in 0.1M PBS for 10 minutes each at room temperature prior to incubating with 1% $OSO_{4(aq)}$ for five min at room temperature. The osmium was rinsed from the slides twice before dehydrating the slides in graded ethanols. The tissue was infiltrated with a thin layer of Epon-812 (Electron Microscopy Sciences, Fort Washington, Pa.) for 5 minutes. Size 0 BEEM capsules (Electron Microscopy Sciences) were filled with embedding medium and inverted onto the slides. The tissue was cured for 48 hours at 65° C. and then allowed to cool for 10 minutes at room temperature. The slides were immersed in liquid nitrogen until the BEEM capsule could be removed from the slide. The resulting block was examined under an inverted light microscope for the presence of embedded tissue. Ultrathin sections were cut with a Diatome® diamond knife on a Sorvall® MT-2B ultramicrotome and examined on a Zeiss® EM 10 electron microscope with an accelerating voltage of 80 kV.

The Results of the Experiments Presented in this Example are now Described

Figure 8:
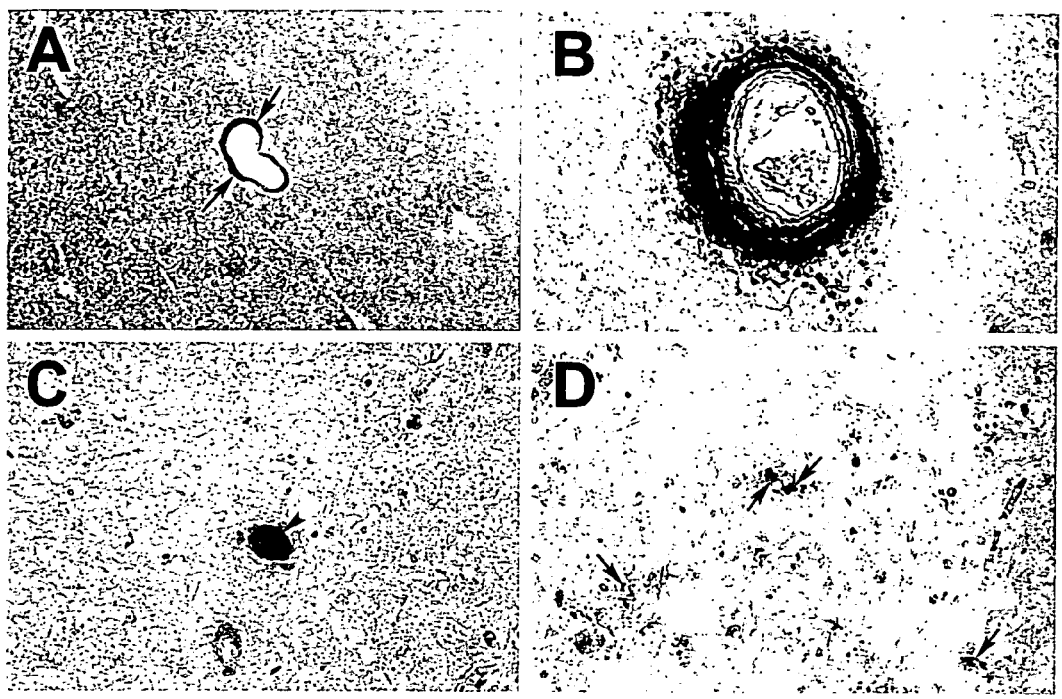
FIG. 8 is a series of images depicting in situ hybridization of AD brains illustrating immunoreactivity with a probe directed to the ompA gene of *C. pneumoniae*. Panel A: Immunoreactivity (arrows) around a blood vessel within the temporal cortex. This labeling profile is consistent with pericyte and/or perivascular macrophage labeling. Bar=250 μm. Panel B: Higher magnification of a different blood vessel labeled with the hybridized probe in the hippocampus of another AD brain. Bar=50 μm. Panel C: A presumptive swollen glial cell (arrowhead) demonstrating immunolabeling within the hippocampus. Bar=50 μm. Panel D: Diffuse, plaque-like immunoreactivity with some cellular labeling (Arrows) within an area of the temporal cortex. Bar=50 μm.
Figure 9:
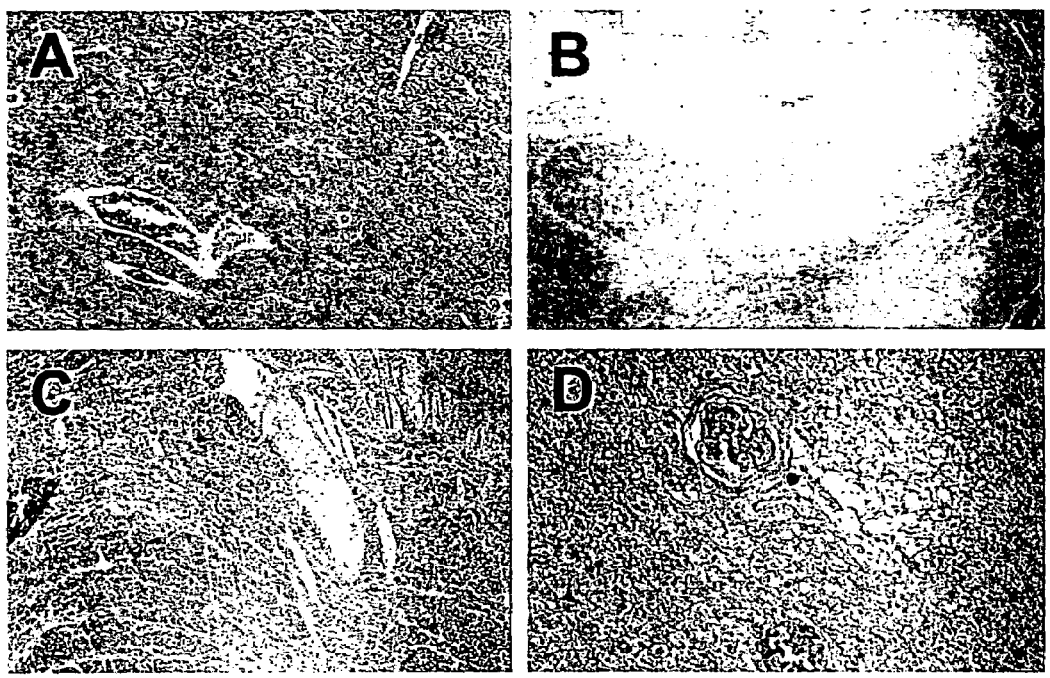
FIG. 9 is a series of images of in situ hybridization of AD and non-AD brains with a DNA probe against the ompA gene of *C. pneumoniae*. Panels A and B: Cerebellar dentate nucleus (A) and cerebellar cortex (B) of two AD brains, areas which usually do not demonstrate AD neuropathology, were not immunoreactive with the probe. Bars=500 μm. Panel C: Negative area of entorhinal cortex of a non-AD brain. Bar=500 μm. Panel D: Temporal cortex of an AD brain not exposed to the ompA probe. Note the non-reactive blood vessel in this section. Bar=50 μm.

In situ hybridization of paraffin embedded AD samples resulted in immunoreactivity consistent with the results which have been previously described herein. Most reactivity was demonstrable only within areas that demonstrated AD neuropathology including the hippocampus and temporal cortex. Although in a minimal number of samples the probe was able to hybridize within the cerebellum, an area which often does not exhibit AD pathology, C. pneumoniae DNA was localized intracellularly within presumptive pericytes (FIG. 8, panel A) and glial cells (FIG. 8, panel C). The probe was immunoreactive not only within particular cells but also extracellular to any defined cellular constituent (FIG. 8, panel B). In some samples, a diffuse immunoreactivity was apparent within the tissue (FIG. 8, panel D). No immunoreactivity was visualized in slides which were incubated with secondary antibody only. It should be noted that the in situ hybridization reactivity was localized/contained to specific focal areas of the tissue sections. In this regard, neither all blood vessels nor all glial cells were immunoreactive. Indeed, there were instances in which one of two adjacent blood vessels was immunoreactive. No significant immunoreactivity was observed in any of the non-AD samples examined, and in all sections background hybridization was minimal (FIG. 9, panels A–D).

Figure 10:
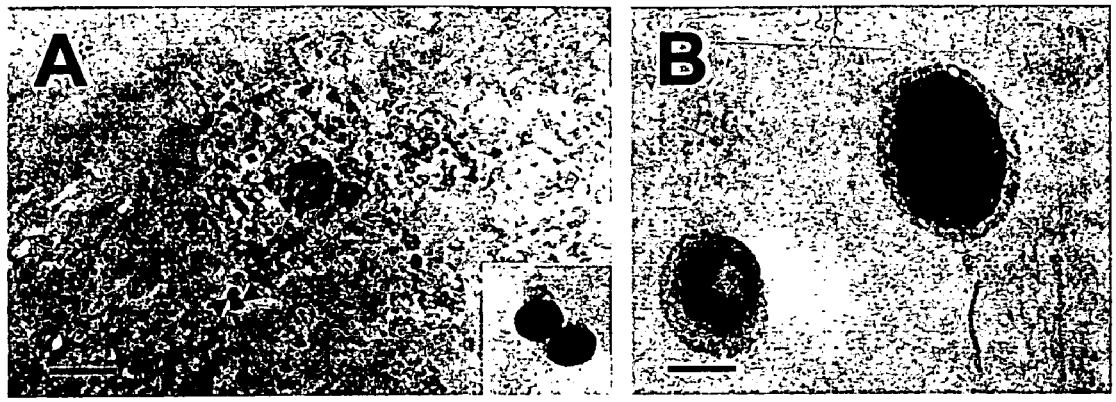
FIG. 10 is a series of images depicting an ultrastructural analyses of AD brain sections processed by in situ hybridization. Panel A: Temporal cortex of an AD brain demonstrating tissue digested by proteinase K. A pair of chlamydial bodies (arrowheads and inset) is clearly visible. Bar=2 μm. Panel B: A higher magnification of two additional chlamydial bodies within the same cortical region of the AD brain shown in Panel A. Bar=0.25 μm.

In order to confirm the presence of the organism in areas of the tissue which stained positive for C. pneumoniae DNA, "in situ-Pop-Off" ultrastructural analyses was performed on the processed tissue sections (FIG. 10, panels A and B). The C. pneumoniae visualized under these conditions were identical to those observed in other experiments described herein. Further, Miyashita et al. (1993, J. Med. Microbiol.38:418–425) have reported that C. pneumoniae can be recognized as spherical or pear shaped and typically resembled the organism seen in the AD brain. The organisms were 0.25–1.2 μm in diameter and some were identified in a state of binary fission.

Figure 11:
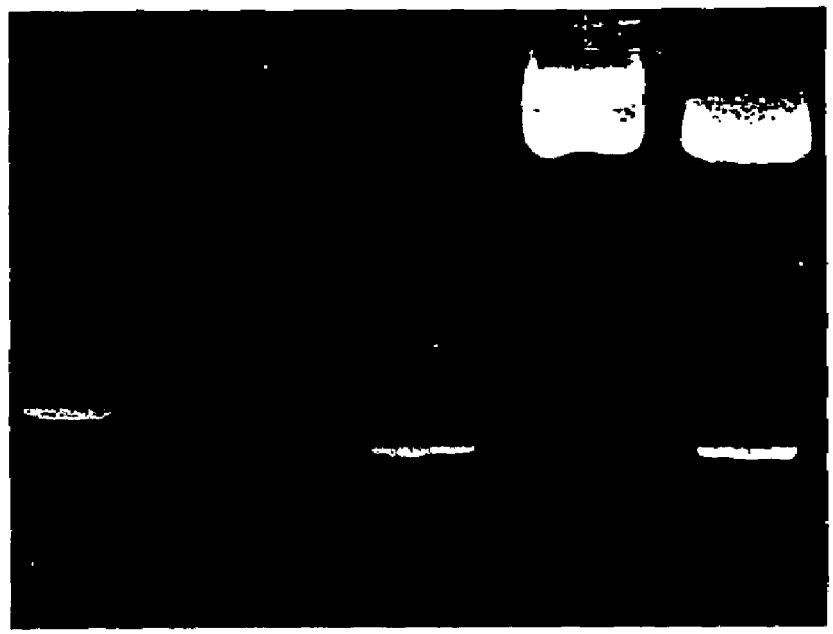
FIG. 11 is an image of a gel depicting the results of a PCR assay performed on nucleic acid obtained from cells. Lane 1: 100 bp standard. Lane 2: PCR using primers against an area of the ompA gene of *C. pneumoniae* on extracted DNA from a human monocyte (THP-1) cell line. Lane 3: PCR using identical primers in Lane 2 on the DNA extracted from the THP-1 cell line infected with the laboratory strain of *C. pneumoniae* (TW-183) showing a 350 bp band. This band was confirmed to be ompA by sequence analysis. The 350 bp PCR product retrieved using the aforementioned primers on DNA extracted from THP-1 cells that were infected with *C. pneumoniae* isolated from AD brains was ligated to a vector and transfected into viable cells for amplification. The excised plasmid vector (uncut: Lane 4) was cut by restriction digestion with ECO-R1 revealing another 350 bp band (Lane 5). This band was also analyzed by sequence analyses and was 100% homologous to the *Chlamydia pneumoniae* ompA gene.

DNA obtained from multiple AD brains obtained from areas demonstrating pathology was extracted and a previously described nested primer system was used to amplify an area of the ompA gene of C. pneumoniae (FIG. 11). It was possible to amplify a 350 bp product by PCR from the AD brains, while the non-AD brains did not exhibit a PCR product. After ligating the PCR product into the pCR 2.1 plasmid, INVαF' E. coli was transfected with the vector. The successfully transfected colonies were cloned in a Qiagen MAXI-PREP kit and ultimately used the restriction endonuclease, EcoRI, to cut the PCR insertion from the plasmid. Again, the gel revealed a 350 bp band which was excised from the agarose gel (FIG. 11). Both the original PCR product and cloned insertion were sequenced and shown to be 100% homologous to the comparable sequence from the ompA gene of C. pneumoniae.

EXAMPLE 3

Infection of Cell Lines of Neurologic Origin with C. pneumoniae TW-183

The data presented in this Example demonstrate that cells of neurologic origin, i.e., glial and neuronal cells, may be infected with the laboratory strain of C. pneumoniae, TW-183.

Figure 12:
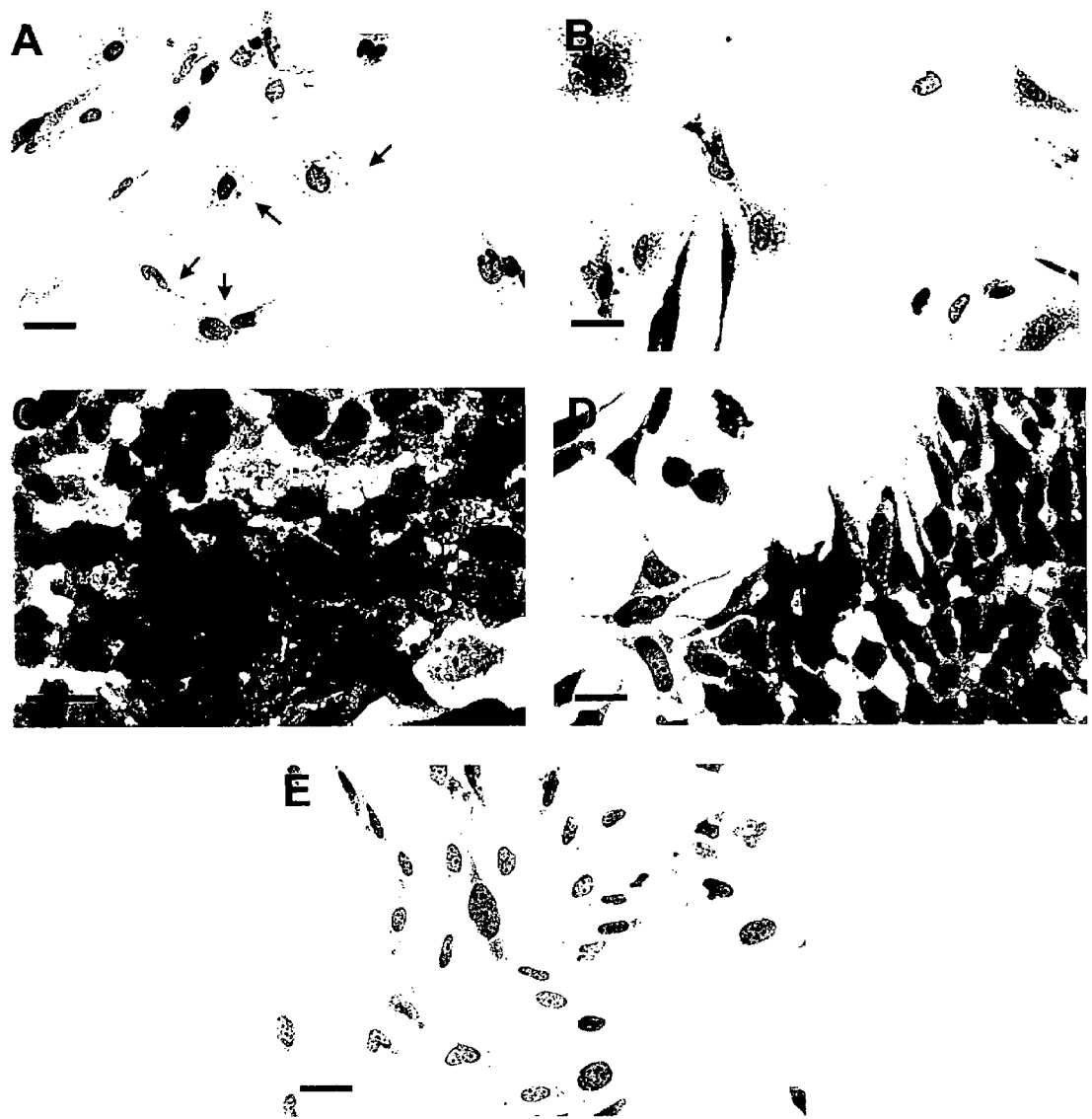
FIG. 12 is a series of images depicting immunohistochemical analysis of cell cultures infected for 3 days with TW-183 demonstrating that glial and neuronal cell lines are susceptible to infection with *C. pneumoniae*. Astrocytoma SW1088 cells immunolabeled with anti-OMP (panel A) and anti-LPS (panel B) antibodies specific to *C. pneumoniae* are also shown. Neuroblastoma SK-N-MC cells immunolabeled with anti-OMP (panel C) and anti-LPS (panel D) antibodies specific to *C. pneumoniae* are also shown. Negative control of uninfected Astrocytoma SW1088 cells immunolabeled with anti-LPS are shown in panel E. Bars=10 μm.

Cells were infected as described elsewhere herein. In FIG. 12 there is described a immunohistochemical analysis of cell cultures infected for three days with TW-183 demonstrating that glial and neuronal cell lines are susceptible to infection with C. pneumoniae. Astrocytoma SW1088 cells immunolabeled with anti-OMP (Panel A) and anti-LPS (Panel B) antibodies specific to C. pneumoniae are shown. Neuroblastoma SK-N-MC cells immunolabeled with anti-OMP (Panel C) and anti-LPS (Panel D) antibodies specific to C. pneumoniae are also shown. Negative control of uninfected astrocytoma SW1088 cells immunolabeled with anti-LPS (Panel E) are also shown. Bars=10 μm. Thus, these cell types can internalize C. pneumoniae and once the bacteria are inside the cells, the bacteria replicate and express bacterial antigens therein. Further, the data also establish that cells of neuronal origin are involved in the pathogenesis of Alzheimer's disease and in addition, these data confirm that cells derived from the mammalian central nervous system may be infected with C. pneumoniae confirming the in situ analyses.

Figure 13:
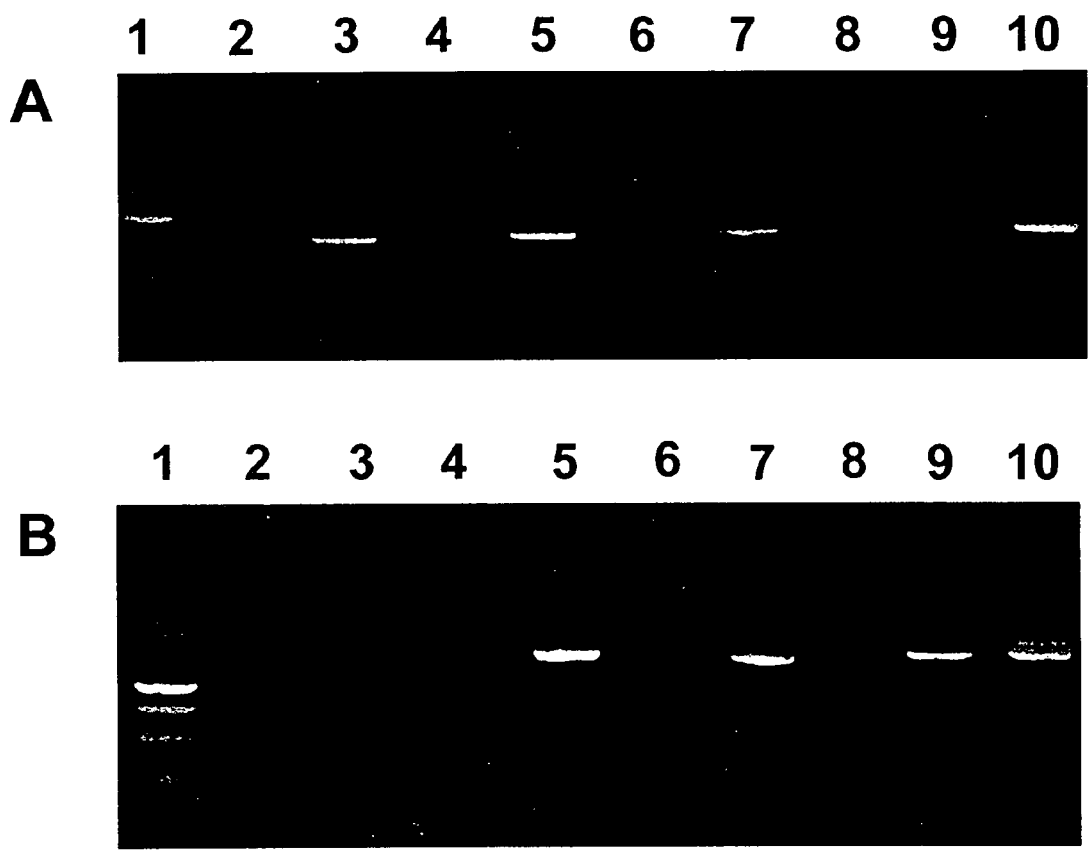
FIG. 13 is an image of a gel depicting RT-PCR using primers specific for the *C. pneumoniae* OMP and 16s rRNA genes. Panel A (OMP), lane 1, 100 bp standards; lane 2, THP-1 cells un-infected, lane 3, THP-1 cells infected with TW-183; lane 4, neuroblastoma SK-N-MC cells un-infected, lane 5, neuroblastoma SK-N-MC cells infected with TW-183; lane 6, Hep2 cells un-infected, lane 7, Hep2 cells infected with TW-183; lanes 8 and 9, astrocytoma cells un-infected; lane 10, positive control of PCR product for OMP(A) from TW-183. Panel B (16s rRNA), lane 1, 100 bp standards; lanes 2 and 3, astrocytoma cells un-infected; lane 4, THP-1 cells un-infected, lane 5, THP-1 cells infected with TW-183; lane 6, neuroblastoma SK-N-MC cells un-infected, lane 7, neuroblastoma SK-N-MC cells infected with TW-183; lane 8, Hep2 cells un-infected, lane 9, Hep2 cells infected with TW- 183; lane 10, positive control of PCR product for 16s rRNA from TW-183.

In FIG. 13 there is shown the results of RT-PCR using primers specific for the C. pneumoniae OMP and 16s rRNA genes. RT-PCR was performed as described elsewhere herein. The image of the gel demonstrates that the cells are infected with C. pneumoniae. Thus, the bacteria were transcriptionally active in these cells establishing that active infection was ongoing in the cels.

EXAMPLE 4

Association of Sézary T-Cell Activating Factor with Involved Alzheimer's Disease Brain Tissue SAF renders non-proliferating quiescent T cells from allogeneic or syngeneic Sézary syndrome patients or healthy donors responsive to IL-2 in the absence of mitogen or antigen (Abrams et al., 1993, Cancer Res. 53:5501–5506). In the present Example, the presence of SAF in involved Alzheimer's brain tissue can be correlated with the presence of C. pneumoniae in the same tissue. Thus, an anti-SAF antibody may be used to detect and diagnose Alzheimer's disease in the brain tissue of a human.

Preparation of SAF

Protein with SAF-like activity was recovered and purified from the SZ-4 cell line for the generation of mAbs inhibitory for SAF bioactivity. Conditioned medium (CM) from the SZ-4 cell line was generated as follows: SZ-4 cells were cultured for 18 hours in RPMI-1640 media containing combinations of 10% FBS alone, 10% FBS and 1 μg/ml phytohemagglutinin (PHA) (Sigma, St. Louis, Mo.), or 10% FBS and phorbol 12-myristate 13-acetate (TPA)(Sigma) and 1 mM ionomycin (Sigma). The cells were then centrifuged, rinsed in media and then cultured for up to 72 hours in serum free RPMI-1640 containing Neutradoma HU (Boehringer Mannheim, Chicago, Ill.).

To characterize fractions for SAF-like activity, and to screen the mAb clones for ability to neutralize SAF activity, SAF bioassays were performed as described herein. Various concentrations of CM from SZ-4 cell lines were added to $1 \times 10^5$ peripheral blood mononuclear cells (PBMC) recovered from the blood of healthy donors along with 10 U/mlrI-2 (Boehringer Mannheim), in 10% FBS-RPMI 1640 media. The samples from these healthy donors were determined by the Red Cross to be sero-negative for HIV-1, HBV, and HTLV. The cells were cultures for 72 hours in a humidified 5% $CO_2$ incubator, with the addition of 1 μCi tritiated thymidine ($^3$H-TdR) (Amersham, Arlington Heights, Ill.) for the final 4 hours in 96 well flat-bottom plates (Costar, Rochester, N.Y.). Cultures were terminated by harvesting onto filter mats (Schleicher & Schuell, Keene, N.H.), and processed for liquid scintillation counting (LSC) by drying and adding 3 ml LS fluid (Econofluor, Dupont, NEN, Wilmington, Del.).

Conditioned media containing SAF was semi-purified by anion exchange chromatography using DE-52 anion exchange resin (Whatman, Clifton, N.J.). Anion exchange purified SZ-4 CM (50 units in 25 µl) was mixed with loading buffer containing 2% SDS and 5% 2-mercaptocthanol, heated to 55° C. for 10 minutes, and elcetrophoresed according to the method of Laemmli in a 10% polyacrylamide gel for 4 hours at a constant current of 25 mA. Three mm slices were cut from the gel and proteins from each gel slice were passively eluted into media containing 10% FBS, to prevent non-specific loss of protein. The SDS was removed by dialysis against BES (5 mM) and the dialysate tested at various concentrations for SAF activity as described. The RF value of each protein fraction was used to determine the apparent molecular mass of SZ-4 SAF. The 28–30 kD SAF active fraction was immunized into Balb/C mice and hybridomas were made. mAbs reactive with the immunogen were screened for SAF inhibitory activity against both the PBMC-derived SAF and cell line-derived SAF. One clone 58.19, an $IgG_3$, was selected, re-cloned, and is named anti-SAF therein.

In initial experiments, anti-SAF antibody was used to inhibit SAF bioactivity in peripheral blood mononuclear cells (PBMC). Twenty five µg/ml of anti-SAF (58.19) was cultured with PMBC from a healthy donor along with various amounts of either phytohemaglutinin (PHA), phorbolmysteric acid (PMA) and ionomycin, cell line-derived (SZ-4 SAF), or PBMC-derived SAF (SZ-1 SAF) in the presence of 15 U/ml recombinant IL-2 (rIL-2) for 72 hours. SZ-1 and SZ-4 cells are PMBCs derived from a patient having Sézary syndrome. A description of tehse cells is found in Abrams et al. (1991, J. Invest. Dermatol. 96:31–37) and in Abrams et al. (1991, J. Immunol. 146:1455–1462). The cells were pulsed with tritiated thymidine for the final 6 hours of incubation. The cells were harvested and the amount of radioactivity contained therein was assessed. The data are presented in FIG. 14 and represent the mean of triplicate cultures. The standard error was less than 10% of the mean.

Figure 14:
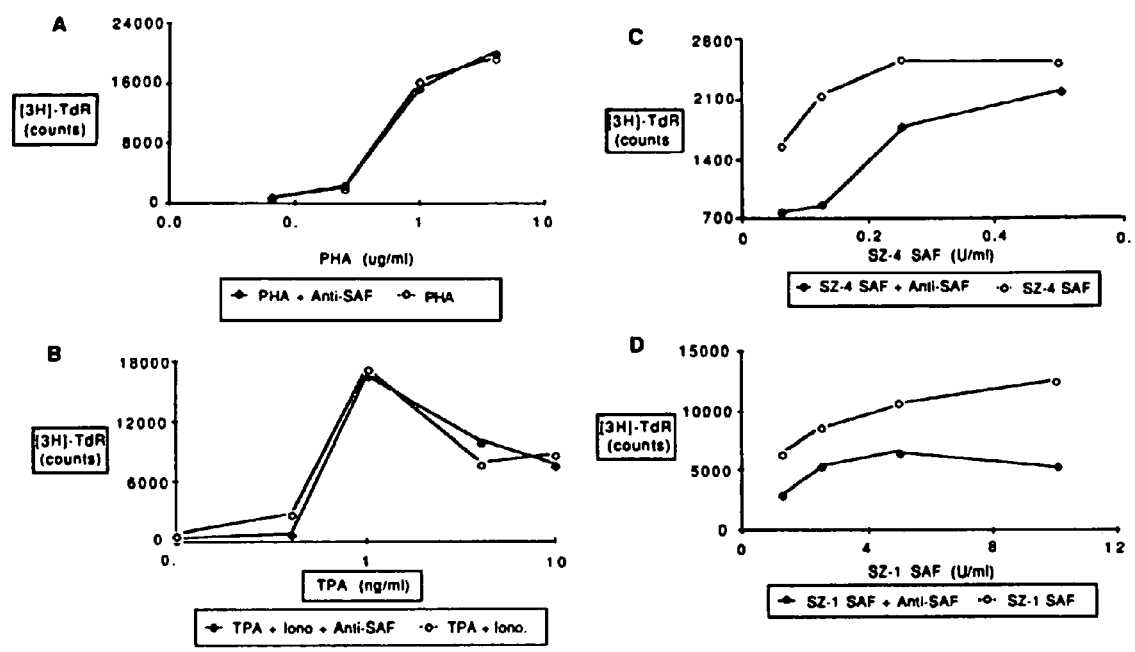
FIG. 14 is a series of graphs depicting inhibition of SAF bioactivity by anti-SAF. Twenty-five μg/ml anti-SAF (58.19) was cultured with PBMC from a healthy donor along with various amounts of either PHA, PMA and ionomycin, cell line-derived (SZ-4-SAF) SAF, or PBMC-derived SAF (SZ-1SAF) in the presence of 15 U/ml rIL-2 for 72 hours. Cells were pulsed with tritiated thymidine for the final 6 hours and harvested and prepared for liquid scintillation counting. The data are the mean of triplicate culture and the standard error was less than 10% of the mean.

In FIG. 14, Panel A, it is evident that anti-SAF antibody did not inhibit PHA-mediated mitogenic activity while, in FIG. 14B, it is evident that anti-SAF antibody did not inhibit TPA and ionomycin-mediated mitogenic activity. PHA stimulates cells at the cell surface, while TPA and ionomycin by pass the cell surface and stimulate cells by directly activating protein kinase C and the release of calcium. The fact that anti-SAF antibody did not inhibit either of these stimulators indicates that anti-SAF antibody-mediated inhibition of SAF activity is specific and is not the result of some general toxicity in the cells. The fact that both the SZ-1 and SZ-4 derived SAF was inhibited indicates that the anti-SAF antibody recognized both the well-defined SAF bioactivity in the original SZ-1 SAF preparation (FIG. 14, Panel D) as well as the SAF activity derived from the SZ-4 cell line (FIG. 14, Panel C) to which the antibody was raised. These data indicate that SAF is present in the AD brain in a region exhibitinh AD neuropathology and it is not present in the AD brain in a region which does not exhibit neuropathology. Second, in serial sections, cells in comparable locations were found to be infected with *C. pneumoniae* supporting the results which indicate that SAF is a *C. pneumoniae*-related antigen.

Figure 15:
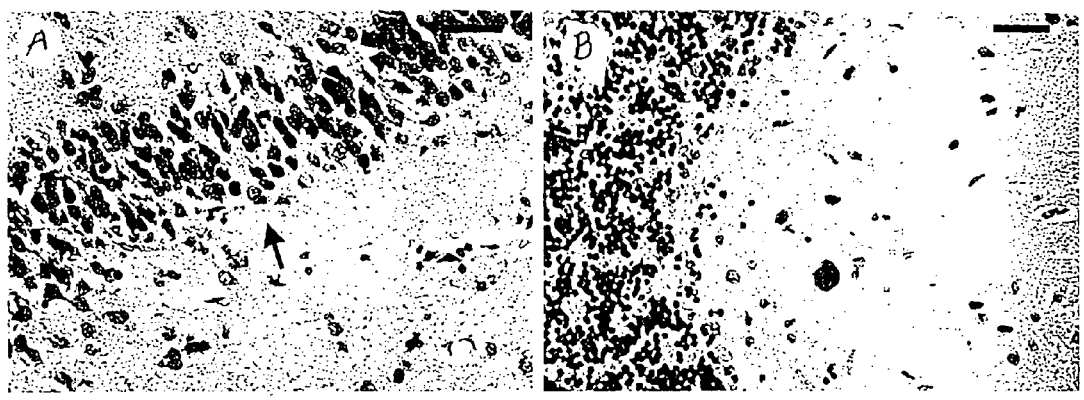
FIG. 15 is a series of images depicting immunohistochemical analysis of anti-SAF (67 μg/ml), anti-*C. pneumoniae* OMP (1:10), and anti-*Chlamydia* LPS (1:10) reactivity in formalin fixed skin and brain tissue. Anti-SAF Immunoreactivity is shown in Panels A and B. Panel A: Anti-SAF reactivity on temporal cortex of a patient with Alzheimer's Disease which was positive for *C. pneumoniae*. Immunolabelling of apparent glial cells in the denate gyrus is depicted by arrows. Panel B: Negative Immunoreactivity of the anti-SAF is shown on a section from the cerebellum (uninvolved) of the same patient. AEC (red) was used in both panels. Bar=50 μm in all panels.

Next, an immunochemical analysis of anti-SAF (67 µg/ml), anti-*C. pneumoniae* OMP (1:10), and anti-*Chlamydia LPS* (1:10) reactivity in formalin fixed skin and brain tissue was performed. Anti-SAF immunoreactivity is shown in panels A and B in FIG. 15. Panel A: Anti-SAF reactivity on the temporal cortex of a patient with Alzheimer's disease which also contains *C. pneumoniae*. Immunolabeling of apparent glial cells in the denate gyrus are depicted by arrows. Panel B: Negative immunoreactivity of the anti-SAF is shown on a section from the uninvolved cerebellum of the same patient. AEC (red) was used in both panels. Bar is 50 µm in each panel.

Figure 16:
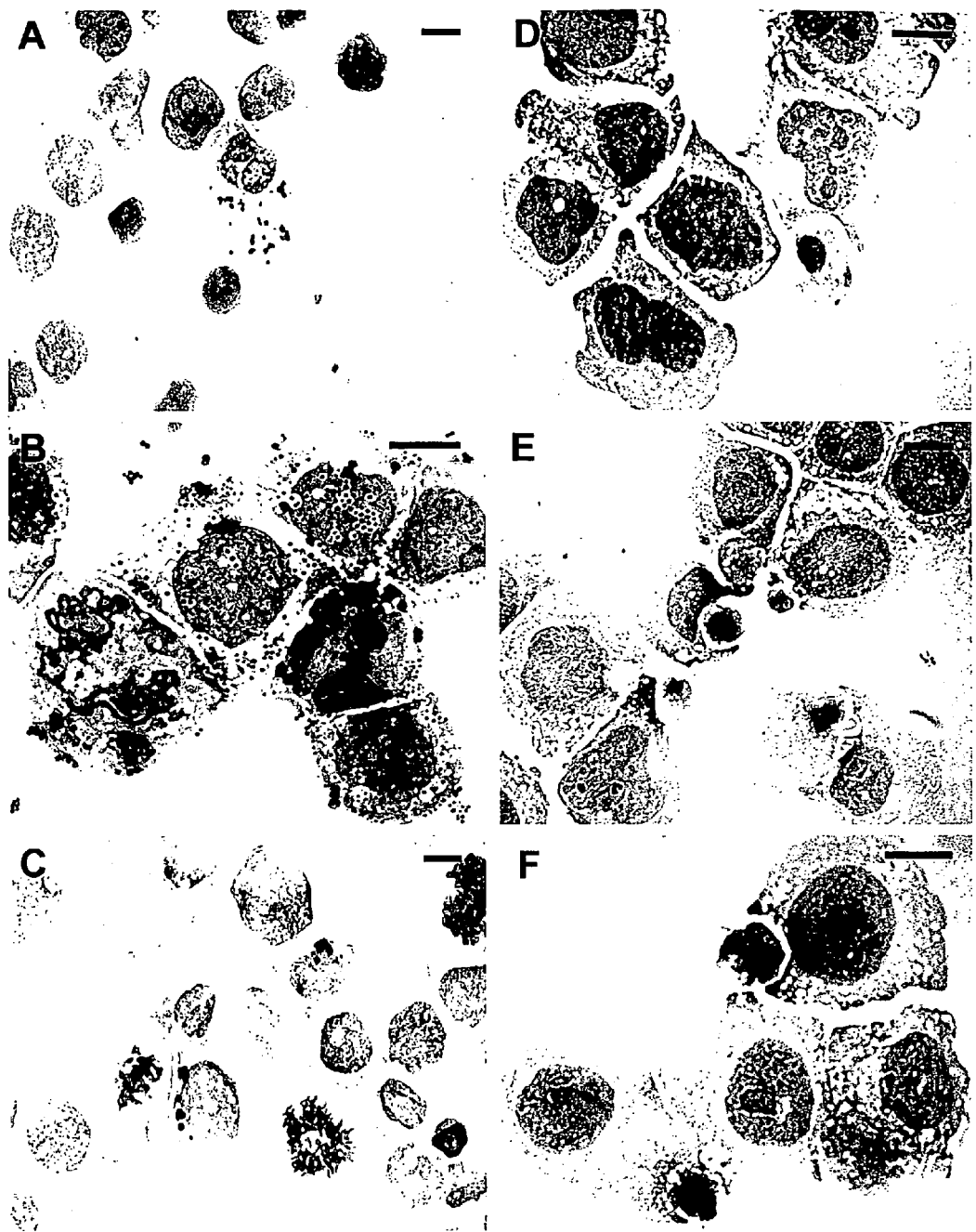
FIG. 16 is a series of images depicting immunolabelling of THP-1 monocyte cell line infected with *C. pneumoniae* isolated from an AD brain and with the laboratory strain of *C. pneumoniae* (TW-183). After culture, THP-1 cells were placed on slides by cytospin and fixed with S.T.F.®. THP-1 cells infected with *C. pneumoniae* isolated from the brain of a patient with AD are in Panels A–C. Immunolabelling of anti-OMP (Panel A), anti-SAF Panel B, and anti-LPS (Panel C) demonstrates reactivity of all these antibodies with inclusions within the infected cells. Panel D contains uninfected THP-1 cells reacted with anti-SAF. THP-1 cells infected for 10 days with the laboratory stain of *C. pneumoniae* TW-183 immunolabelled with anti-OMP (Panel E) or anti-SAF (Panel F) contains cells with inclusions diffusely staining with these antibodies. Bar s=10 μm in all Panels.

The THP-1 monocyte cell line was infected with *C. pneumoniae* which was isolated from an AD brain and with the laboratory strain of this organism, TW-183. After culture, THP-1 cells were placed on slides by cytospin and were fixed with (Streck Tissue Fixative (S.T.F.®; Streck, Omaha, Nebr.) and were analyzed for the presence of SAF and *C. pneumoniae* using various antibodies as described. The results of this experiment are shown in FIG. 16. THP-1 cells infected with *C. pneumoniae* isolated from the brain of an AD patient are shown in panels A–C. Immunolabeling of anti-OMP (Panel A), anti-SAF (Panel B) and anti-LPS (Panel C) demonstrates immunoreactivity of all of these antibodies with inclusions in the infected cells. Panel D contains uninfected THP-1 cells reacted with anti-SAF antibody. THP-1 cells infected for ten days with the laboratory strain of *C. pneumoniae* TW-183 immunolabeled with anti-OMP (Panel E) or anti-SAF (Panel F) contains cells with inclusions which diffusely stain with these antibodies. Bars are 10 µm in all Panels.

Figure 17:
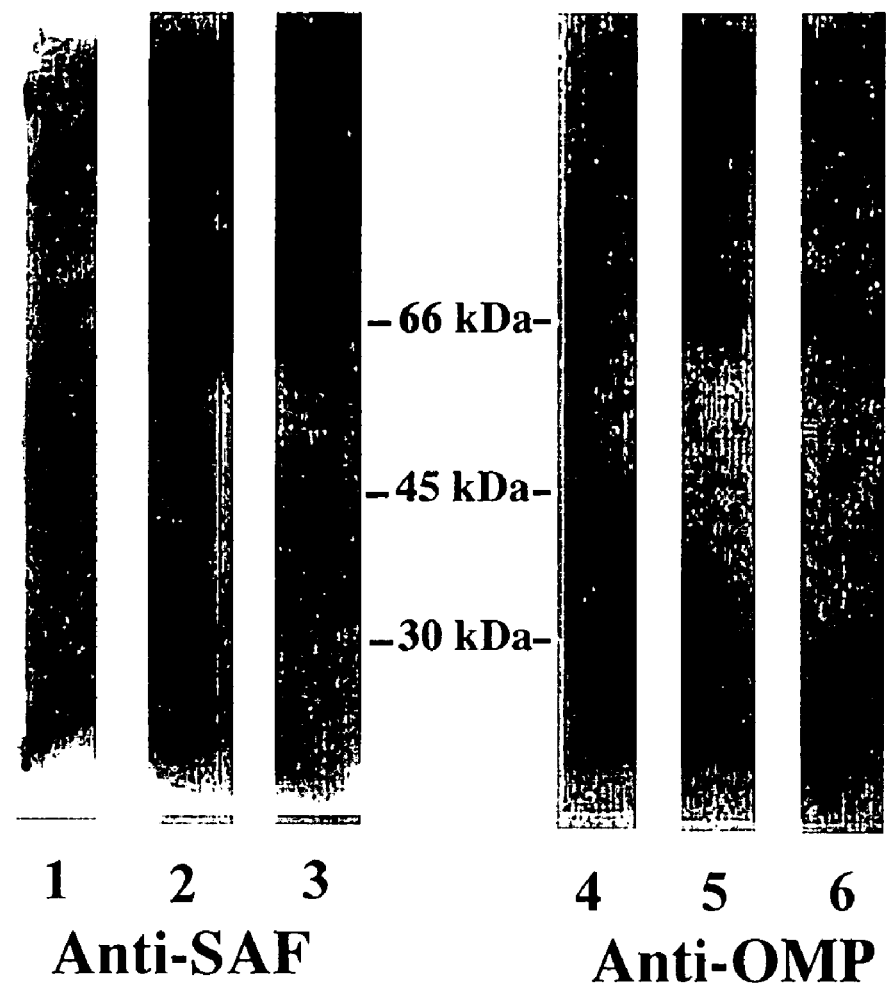
FIG. 17 is a two images depicting immunoblot analysis of anti-SAF and anti-OMP reactivity to *C. pneumoniae* proteins. Anti-SAF (1:100) (lanes 1–3) and anti-OMP (1.5) (Lanes 4–6) reactivity to lysates made with uninfected THP-1 cells (Lanes 1 and 4), *C. pneumoniae* TW-183 from ATCC (Lanes 2 and 5) and THP-1 cells infected with *C. pneumoniae* from an AD brain (3 and 6). Proteins were electrophoresed and transferred to nitrocellulose and tested from reactivity. Antibody binding was detected with anti-mouse conjugated with HRP. Secondary antibody binding was revealed by Enhanced Chemiluminescence and exposed to Hyperfilm-ECL for 10 minutes.

Immunoblot analysis of anti-SAF and anti-OMP reactivity to *C. pneumoniae* proteins was performed. The results of this experiment are shown in FIG. 17. Lysates were made from ultracentrifuged elementary bodies which were obtained from infected cultures collected for several days (more than seven days) as well as from infected cell pellets. Control pellets were generated from uninfected THP-1 cells. Infections were as described elsewhere herein, using isolates from various brains. Anti-SAF (1:100; lanes 1–3) and anti-OMP (1:5; lanes 4–6) reactivity to lysates made from uninfected THP-1 cells (lanes 1 and 4), *C. pneumoniae* TW-183 (lanes 2 and 5) and THP-1 cells infected with *C. pneumoniae* obtained from an AD brain (lanes 3 and 6) are shown. The proteins were electrophoresed and transferred to nitrocellulose and were tested for reactivity. Antibody binding was detected using anti-mouse conjugated with horse radish peroxidase. Secondary antibody binding was revealed by Enhanced Chemiluminescence and exposed to Hyperfilm-ECL for 10 minutes.

Figure 18:
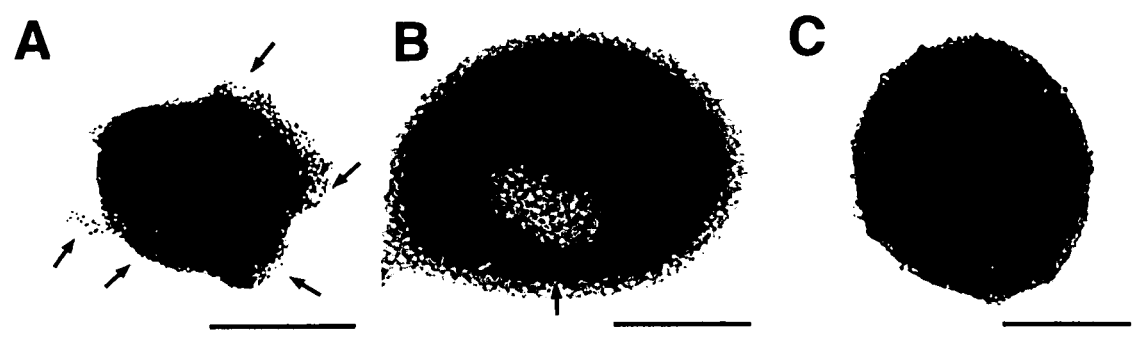
FIG. 18 is a series of images depicting negative staining combined with immunoelectron microscopy of *C. pneumoniae*. Pellets (11,000×g) from culture supernatants of THP-1 cells infected with *C. pneumoniae* isolated from a patient with AD, and cultured for 7 days, were absorbed onto carbon-coated copper EM grids. Grids were exposed to the primary antibodies, incubated, and subsequently incubated with secondary anti-mouse antibody conjugated to 5 or 15 nm colloidal gold particles. Negative staining of the grids was accomplished with 2.0% uranyl acetate. The grids were examined at 80 kV on a Zeiss EM-10 electron microscope. Panel A: 8 to 10 gold particles (5 nm) are bound to the anti-SAF labeled bacterium, examples of which are depicted with arrows. Panel B: An area of a bacterium apparently rich in OMP protein (arrow) is exposed and labeled with gold particles (5 nm). Panel C: A bacterium reacted with anti-LPs demonstrates heavy labeling with many 5 nm gold particles bound to its surface. Bars=0.5 μm for panels B & C. Bar=0.75 μm for Panel A.

Negative staining combined with immunoelectronmicroscopy of *C. pneumoniae* was also performed. The results of this experiment are shown in FIG. 18. Pellets of culture supernatants (centrifuged at 11,000×g) of THP-1 cells infected with *C. pneumoniae* isolated from an AD patient and cultured for 7 days, were adsorbed onto carbon-coated copper EM grids. The grids were exposed to the primary antibodies, incubated and were subsequently incubated with secondary anti-mouse antibody conjugated to 5 or 15 nm colloidal gold particles. Negative staining of the grids was accomplished with 2.0% uranyl acetate. The grids were examined at 80 kV on a Zeiss EM-10 electron microscope. Panel A: 8 to 10 gold particles (5 nm) are bound to the anti-SAF labeled bacterium, examples of which are shown by the arrows. Panel B: An area of a bacterium apparently rich in OMP protein (arrow) is exposed and labeled with gold particles (5 nm). Panel C: A bacterium reacted with anti-LPS illustrates heavy labeling with many 5 nm gold particles bound to it's surface. The bar is 0.5 µm in the case of Panels B and C. The bar is 0.75 µm in the case of Panel A.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating Alzheimer's disease in a living being comprising administering to the living being a therapeutic amount of an antimicrobial agent, wherein the antimicrobial agent is a macrolide, and further wherein the macrolide is selected from the group consisting of azithromycin, clarithromycin, dirithromycin, erythromycin and troleandomycin.

2. The method of claim 1 wherein the macrolide is azithromycin.

3. A method of treating Alzheimer's disease in a living being comprising administering to the living being a therapeutic amount of an anti-microbial agent, wherein the antimicrobial agent is a fluoroquinolone.

4. The method of claim 3 wherein the fluoroquinolone is selected from the group consisting of ciprofloxacin and ofloxacin.

5. A method of treating Alzheimer's disease in a living being comprising administering to the living being a therapeutic amount of an anti-microbial agent, wherein the antimicrobial agent is a sulfonamide.

6. A method of treating Alzheimer's disease in a living being comprising administering to the living being a therapeutic amount of an anti-microbial agent, wherein the antimicrobial agent comprises both sulfamethoxazole and trimethoprim.

7. The method of claim 4 wherein the antimicrobial agent is ciprofloxacin.

8. The method of claim 4 wherein the antimicrobial agent is ofloxacin.

9. A method of treating Alzheimer's disease in a living being comprising administering to the living being a therapeutic amount of an anti-microbial agent and an anti-inflammatory agent wherein the antimicrobial agent is a macrolide, and further wherein the macrolide is selected from the group consisting of azithromycin, clarithromycin, dirithromycin, erythromycin and troleandomycin.

10. The method of claim 9 wherein the macrolide is azithromycin.

11. A method of treating Alzheimer's disease in a living being comprising administering to the living being a therapeutic amount of an anti-microbial agent and an anti-inflammatory agent wherein the antimicrobial agent is a fluoroquinolone.

12. The method of claim 11 wherein the fluoroquinolone is selected from the group consisting of ciprofloxacin and ofloxacin.

13. A method of treating Alzheimer's disease in a living being comprising administering to the living being a therapeutic amount of an anti-microbial agent and an anti-inflammatory agent wherein the antimicrobial agent is a sulfonamide.

14. A method of treating Alzheimer's disease in a living being comprising administering to the living being a therapeutic amount of an anti-microbial agent and an anti-inflammatory agent wherein the antimicrobial agent comprises both sulfamethoxazole and trimethoprim.

15. The method of claim 12 wherein the antimicrobial agent is ciprofloxacin.

16. The method of claim 12 wherein the antimicrobial agent is ofloxacin.

* * * * *